US012192609B2

(12) United States Patent
Hayashi et al.

(10) Patent No.: US 12,192,609 B2
(45) Date of Patent: Jan. 7, 2025

(54) LIGHT SOURCE DEVICE AND ENDOSCOPE SYSTEM

(71) Applicant: HOYA CORPORATION, Tokyo (JP)

(72) Inventors: Yoshihiro Hayashi, Tokyo (JP); Yoshiyuki Niijima, Tokyo (JP); Yukari Akino, Tokyo (JP); Shinya Shimotashiro, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 138 days.

(21) Appl. No.: 18/024,578

(22) PCT Filed: Sep. 22, 2021

(86) PCT No.: PCT/JP2021/034781

§ 371 (c)(1),
(2) Date: Mar. 3, 2023

(87) PCT Pub. No.: WO2022/091649

PCT Pub. Date: May 5, 2022

(65) Prior Publication Data

US 2023/0319386 A1 Oct. 5, 2023

(30) Foreign Application Priority Data

Oct. 27, 2020 (JP) ................................. 2020-179317

(51) Int. Cl.
*A61B 1/06* (2006.01)
*A61B 1/045* (2006.01)
(Continued)

(52) U.S. Cl.
CPC ........... *H04N 23/555* (2023.01); *H04N 23/56* (2023.01); *H04N 23/73* (2023.01)

(58) Field of Classification Search
CPC ...... H04N 23/555; H04N 23/56; H04N 23/73; H04N 23/74; A61B 1/045; A61B 1/0655;
(Continued)

(56) References Cited

U.S. PATENT DOCUMENTS 8,785,833 B2 6/2014 Yabe et al.
9,057,499 B2 * 6/2015 Livesay ................. F21S 8/046
(Continued)

FOREIGN PATENT DOCUMENTS

JP 5379932 B1 12/2013
JP 2017-510348 A 4/2017
(Continued)

OTHER PUBLICATIONS

Supplementary European Search Report issued in European Patent Office application No. 21885768.8, dated Jul. 11, 2024.
(Continued)

*Primary Examiner* — Philip P. Dang
(74) *Attorney, Agent, or Firm* — GREENBLUM & BERNSTEIN, P.L.C.

(57) ABSTRACT

A light source device that generates illumination light, the light source device including: a plurality of semiconductor light emitting elements that emit light beams having different wavelength bands; and a control unit that controls a light emission profile of the plurality of semiconductor light emitting elements and drives the plurality of semiconductor light emitting elements, in which the light emission profile includes a strong light emission period in which light emission is performed with a predetermined light intensity and a weak light emission period in which light emission is performed with a light intensity weaker than the predetermined light intensity, and the control unit executes a restoration control process of converting into a light emission amount in the strong light emission period while maintain-
(Continued)

ing a total amount of the light emission amount in the strong light emission period and the light emission amount in the weak light emission period constant.

15 Claims, 14 Drawing Sheets

(51) Int. Cl.

| | |
|---|---|
| ***H04N 23/50*** | (2023.01) |
| ***H04N 23/56*** | (2023.01) |
| ***H04N 23/73*** | (2023.01) |

(58) Field of Classification Search
CPC .. A61B 1/0684; A61B 1/0638; G02B 23/2461
See application file for complete search history.

(56) References Cited

U.S. PATENT DOCUMENTS

| | | | | |
|---|---|---|---|---|
| 9,119,544 | B2 | 9/2015 | Dai et al. | |
| 9,179,074 | B2 * | 11/2015 | Yasuda | A61B 1/000094 |
| 10,254,223 | B2 * | 4/2019 | Kjaerulff | G02B 27/0961 |
| 10,595,708 | B2 * | 3/2020 | Kojima | A61B 1/00006 |
| 10,928,518 | B2 * | 2/2021 | Yoshida | G01S 7/4802 |
| 11,612,041 | B2 * | 3/2023 | Kojima | A61B 5/0051 |
| 2012/0078044 | A1 * | 3/2012 | Yamaguchi | A61B 1/063<br>600/109 |
| 2014/0014820 | A1 | 1/2014 | Yabe et al. | |
| 2014/0203170 | A1 | 7/2014 | Ono et al. | |
| 2017/0095297 | A1 | 4/2017 | Richmond et al. | |
| 2017/0257619 | A1 | 9/2017 | Kashima | |
| 2018/0140173 | A1 | 5/2018 | Nishio | |
| 2019/0008372 | A1 | 1/2019 | Tanaka et al. | |
| 2020/0297184 | A1 | 9/2020 | Kono | |
| 2021/0113075 | A1 | 4/2021 | Ito et al. | |
| 2023/0319386 | A1 * | 10/2023 | Hayashi | H04N 23/73<br>348/68 |
| 2023/0363630 | A1 * | 11/2023 | Hayashi | G02B 27/0905 |

FOREIGN PATENT DOCUMENTS

| | | | |
|---|---|---|---|
| JP | 6239220 | B1 | 11/2017 |
| JP | 2018-182580 | A | 11/2018 |
| JP | 2020-151090 | A | 9/2020 |
| WO | 2013/157368 | A1 | 10/2013 |
| WO | 2017/013780 | A1 | 1/2017 |
| WO | 2020/012563 | A1 | 1/2020 |

OTHER PUBLICATIONS

International Search Report issued in International Bureau of WIPO Patent Application No. PCT/JP2021/034781, dated Nov. 30, 2021, along with an English translation thereof.

Office Action issued in Japanese application No. 2020-179317, dated Jun. 4, 2024, along with an English translation thereof.

* cited by examiner

LIGHT SOURCE CONFIGURATION EXAMPLE USING LEDS HAVING DIFFERENT LIGHT DISTRIBUTIONS

LIGHT SOURCE DEVICE AND ENDOSCOPE SYSTEM

TECHNICAL FIELD

The present disclosure relates to a light source device and an endoscope system.

BACKGROUND ART

A normal endoscope device equipped with a rolling shutter type image sensor executes pseudo-global exposure to avoid the occurrence of an undesirable phenomenon caused by a rolling shutter, such as distortions and artifacts, by turning off a light source in a valid pixel readout period (rolling shutter period) of the image sensor, and turning on the light source in a period other than this period (pseudo-global exposure period) (pulsed light emission control).

On the other hand, when the light source is completely turned off during the rolling shutter period, the amount of light becomes insufficient depending on an object (observation target site), and a satisfactory image cannot be acquired. In order to solve the insufficiency of the light amount, for example, Patent Literatures 1 to 3 and the like describe light source control in which a part of a rolling shutter period is included in a pulsed light emission period.

CITATION LIST

Patent Literature

Patent Literature 1: JP 2018-182580 A
Patent Literature 2: JP 5379932 B2
Patent Literature 3: JP 6239220 B2

SUMMARY OF INVENTION

Technical Problem

However, when the light source control as described in Patent Literatures 1 to 3 is executed, screen brightness unevenness, horizontal stripes, and the like are caused by a difference in exposure time between lines in adjacent frames. There is the problem that the brightness unevenness and the horizontal stripes move up and down on a display screen to obstruct the view due to a change in the pulsed light emission period between the frames. In addition, in a case where offset light emission is performed during the rolling shutter period in order to solve the insufficiency of the light amount, the offset light emission performed at a certain high level results in an unnatural image generated as if by double exposure of a long-time exposure image and a high-speed exposure image.

The present disclosure has been made in view of such a situation, and proposes a technique of ensuring a sufficient amount of light while avoiding the occurrence of distortions and artifacts caused by a rolling shutter, and making brightness unevenness and horizontal stripes less noticeable even when a change in a pulsed light emission organ occurs over a rolling shutter period.

Solution to Problem

In order to solve the above problem, the present embodiment proposes a light source device that generates illumination light with which an object is irradiated, the light source device including: a plurality of semiconductor light emitting elements that emit light beams having different wavelength bands from each other; and a control unit that controls a light emission profile of the plurality of semiconductor light emitting elements and drives the plurality of semiconductor light emitting elements, in which the light emission profile includes a strong light emission period in which light emission is performed with a predetermined light intensity and a weak light emission period in which light emission is performed with a light intensity weaker than the predetermined light intensity, and the control unit executes a restoration control process of converting a light emission amount in the weak light emission period into a light emission amount in the strong light emission period while maintaining a total amount of the light emission amount in the strong light emission period and the light emission amount in the weak light emission period constant.

In addition, the present embodiment proposes an endoscope system that inserts an endoscope into an observation target and acquires an image of an object, the endoscope system including: a plurality of semiconductor light emitting elements that emit light beams having different wavelength bands from each other; an image sensor that irradiates the object with illumination light and detects reflected light from the object to generate an image signal; a processor that processes the image signal to generate the image of the object and displays the image on a monitor; a main control unit that generates a control signal for controlling a light emission profile of the plurality of semiconductor light emitting elements on the basis of the image signal; and a light source control unit that receives the control signal from the main control unit and drives the plurality of semiconductor light emitting elements with a drive signal according to the light emission profile, in which the light emission profile includes a strong light emission period in which light emission is performed with a predetermined light intensity and a weak light emission period in which light emission is performed with a light intensity weaker than the predetermined light intensity, and the main control unit determines the light emission profile by executing a restoration control process of converting a light emission amount in the weak light emission period into a light emission amount in the strong light emission period while maintaining a total amount of the light emission amount in the strong light emission period and the light emission amount in the weak light emission period constant.

Further features related to the present disclosure will become apparent from the description of the present specification and the accompanying drawings. The present disclosure is achieved and implemented by elements and combinations of various elements and by modes of the following detailed description and the appended claims.

It is to be understood that the description in this specification is merely exemplary and is not intended to limit the significance of the claims or the application in any way.

Advantageous Effects of Invention

According to the present disclosure, it is possible to ensure a sufficient amount of light while avoiding the occurrence of distortions and artifacts caused by a rolling shutter, and to make brightness unevenness and horizontal stripes less noticeable even when a change in a pulsed light emission organ occurs over a rolling shutter period.

DESCRIPTION OF EMBODIMENTS

Hereinafter, embodiments of the present disclosure will be described with reference to the drawings. In the following, an endoscope system will be described as an embodiment of the present disclosure.

An observation target site in the endoscope system is, for example, respiratory organs or digestive organs. Examples of the respiratory organs include the lungs, the bronchus, the ears, the nose, and the throat. Examples of the digestive organs include the large intestine, the small intestine, the stomach, the esophagus, the duodenum, the uterus, and the bladder. In a case of observing the target sites as described above, it is more effective to utilize an image in which a specific biological structure is emphasized.

<Configuration of Endoscope System>

Figure 1:
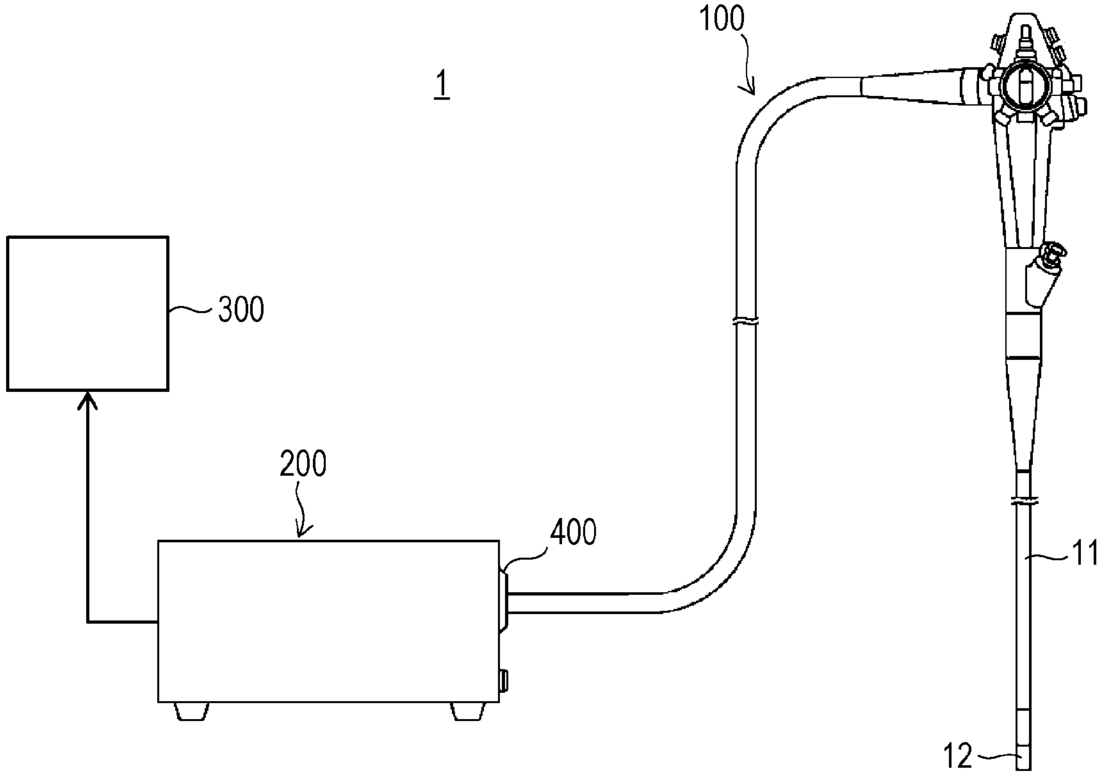
FIG. 1 is a diagram illustrating an overall appearance example of an endoscope system according to the present embodiment.
Figure 2:
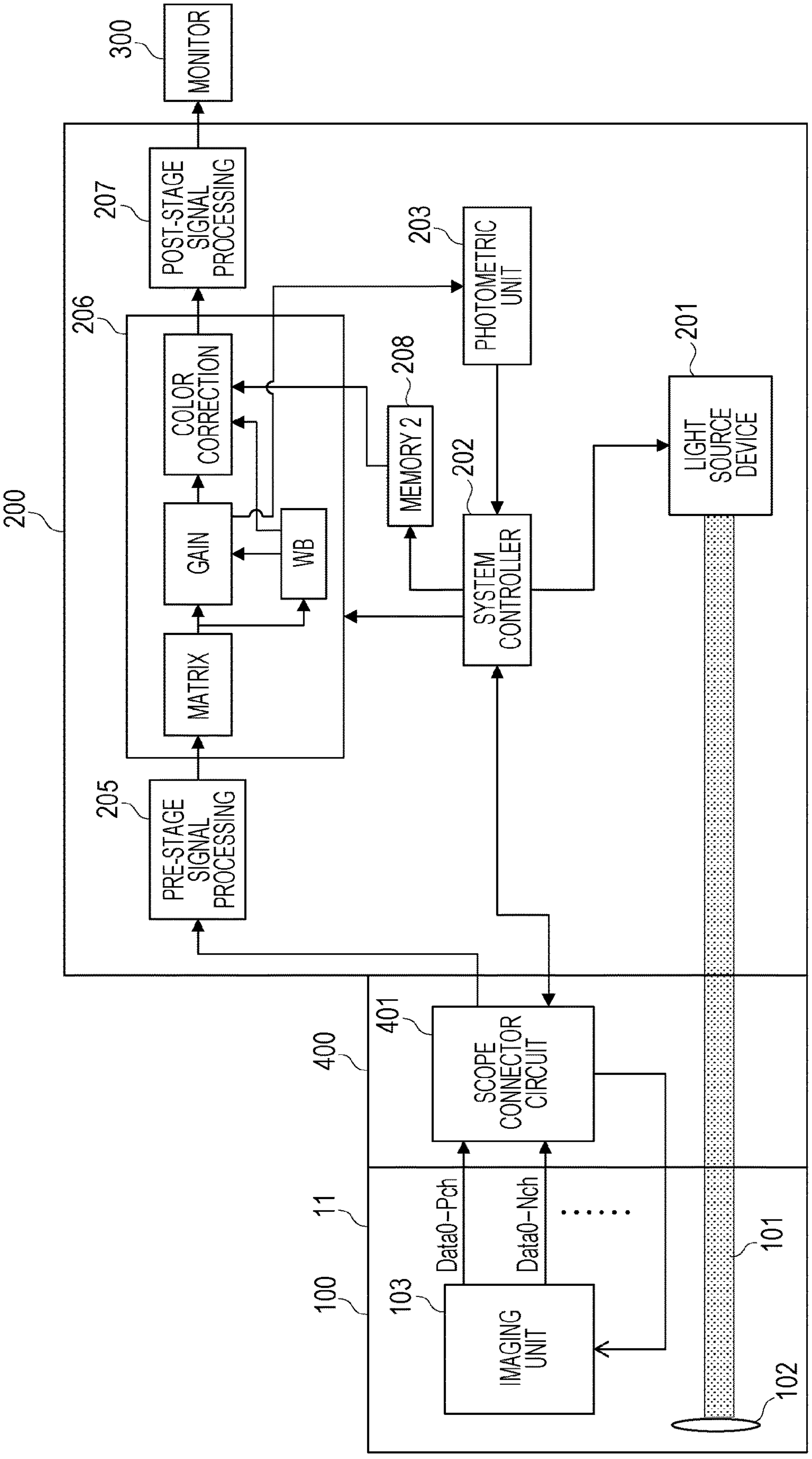
FIG. 2 is a diagram illustrating a schematic internal configuration example of the endoscope system according to the present embodiment.

FIG. 1 is a diagram illustrating an overall appearance example of the endoscope system of the present embodiment, and FIG. 2 is a diagram illustrating a schematic internal configuration example of the endoscope system of the present embodiment. An endoscope system 1 includes an endoscope device (electronic scope) 100, a processor 200, and a monitor 300. Note that a scope connector (which may hereinafter be simply referred to as a "connector") 400 including a connector circuit according to a feature of the present embodiment is provided at a processor-side end portion of the endoscope device 100.

The endoscope device 100 includes an elongated tubular insertion portion 11 configured to be inserted into a subject. The endoscope device 100 includes, for example, a light carrying bundle (LCB) 101 for guiding irradiation light from a light source device 201 to be described later, a light distribution lens 102 provided at an emission end of the LCB 101, an imaging unit 103 that receives return light from an irradiated portion (observation site) via an objective lens (not illustrated), a driver signal processing circuit 105 that drives the imaging unit 103, and a first memory 106.

The irradiation light from the light source device 201 enters the LCB 101 and propagates by repeating total reflection in the LCB 101. The irradiation light (illumination light) propagating in the LCB 101 is emitted from the emission end of the LCB 101 disposed in a distal tip 12 of the insertion portion 11, and irradiates the observation site through the light distribution lens 102. The return light from the irradiated portion forms an optical image by each pixel on a light receiving surface of the imaging unit 103 via the objective lens.

The imaging unit 103 is disposed in the distal tip 12 of the insertion portion 11, and a complementary metal oxide semiconductor (CMOS) image sensor that is a rolling shutter type image sensor can be used. The imaging unit 103 accumulates the optical image (return light from a living tissue) formed by each pixel on the light receiving surface, as charges corresponding to the amount of light, and generates and outputs image signals of R, G, and B. Note that the imaging unit 103 is not limited to the CMOS image sensor, and may be replaced with another type of imaging device as long as the imaging device is based on a rolling shutter method. A signal output from the imaging unit 103 is processed by a scope connector circuit 401 provided in the scope connector 400 as described later.

The processor 200 is a device that integrally includes a signal processing device that processes a signal from the endoscope device 100 and a light source device that irradiates, via the endoscope device 100, a body cavity having difficulty in receiving natural light. In another embodiment, the signal processing device and the light source device may be provided separately. The processor 200 includes the light source device 201, a system controller 202, a photometric unit 203, a pre-stage signal processing circuit 205, a color conversion circuit 206, a post-stage signal processing circuit 207, and a second memory 208.

The processor 200 may include an operation panel (not illustrated). The operation panel may have various configurations. Examples of a specific configuration of the operation panel include a hardware key for each function mounted on a front surface of the processor 200, a touch panel type graphical user interface (GUI), and a combination of a hardware key and a GUI. An operator (operator) can perform a mode switching operation described later with the operation panel.

The photometric unit 203 acquires luminance information of an image signal obtained by imaging from a gain circuit included in the color conversion circuit 206, compares the acquired luminance information with a predetermined correct luminance value (for example, the information of the correct luminance value can be stored in advance in an internal memory (not illustrated) of the photometric unit 203), and notifies the system controller 202 of the comparison result (whether the current luminance value is correct, high, or low).

The system controller 202 executes various programs stored in a memory (not illustrated) and integrally controls the entire endoscope system 1. The system controller 202 controls the operations and timings of various circuits in the processor 200 by using a control signal so as to perform processing suitable for the endoscope device 100 connected to the processor 200. Note that the system controller 202 may be connected to the above-described operation panel.

In addition, the system controller 202 receives the comparison result with the correct luminance value from the photometric unit 203, determines whether to maintain current exposure (exposure), whether to increase the exposure (including a level value to be increased), or whether to decrease the exposure (including a level value to be decreased), and outputs an exposure control signal to the light source device 201.

Furthermore, the system controller 202 changes each of operation of the endoscope system 1 and parameters for each of the operation in accordance with an operator's instruction input from the operation panel. For example, when the operator selects an observation mode with the operation panel (mode switching operation), the system controller 202 outputs a mode selection signal for causing a light source corresponding to the observation mode to emit light, to the light source device 201. As described later, for example, a plurality of light emitting diodes (LEDs) that emit light beams having different wavelength bands from each other can be used as the light source device 201 (see FIG. 3). When the operator selects the observation mode (for example, a normal observation mode, a special light observation mode, a SatO2 mode, and the like) by, for example, operating a mode selection switch provided in the processor 200, the system controller 202 generates the mode selection signal corresponding to the selected mode and supplies the mode selection signal to a light source control unit 2016 of the light source device 201 (see FIG. 3). The light source control unit 2016 determines a combination of LEDs to emit light and their intensities and light amounts on the basis of the mode selection signal (for example, the combination of LEDs to emit light corresponding to the mode selection signal and the like are stored in advance in an internal memory (not illustrated)), and outputs a necessary LED control signal to each of LEDs 2011 to 2015. Each of the LEDs 2011 to 2015 emits a light beam having each wavelength band on the basis of the LED control signal supplied from the light source control unit 2016. The emitted light beams are combined by a cross prism to generate irradiation light (combined light).

Data communication between the endoscope device 100 and the processor 200 may use a wired electric communication scheme or an optical wireless communication scheme.

As illustrated in FIG. 2, the endoscope device 100 and the processor 200 are connected via the scope connector 400. The connector 400 includes an LCB constituting a part of the LCB 101 continuing from the processor 200 to the endoscope device 100, and the scope connector circuit 401. Note that the scope connector circuit 401 is provided in the scope connector 400 in the present embodiment, but is not necessarily provided in the scope connector 400. For example, a circuit corresponding to the scope connector circuit 401 may be provided in a connector unit on the processor 200 side or inside the processor 200.

<Internal Configuration Example of Light Source Device 201>

Figure 3:
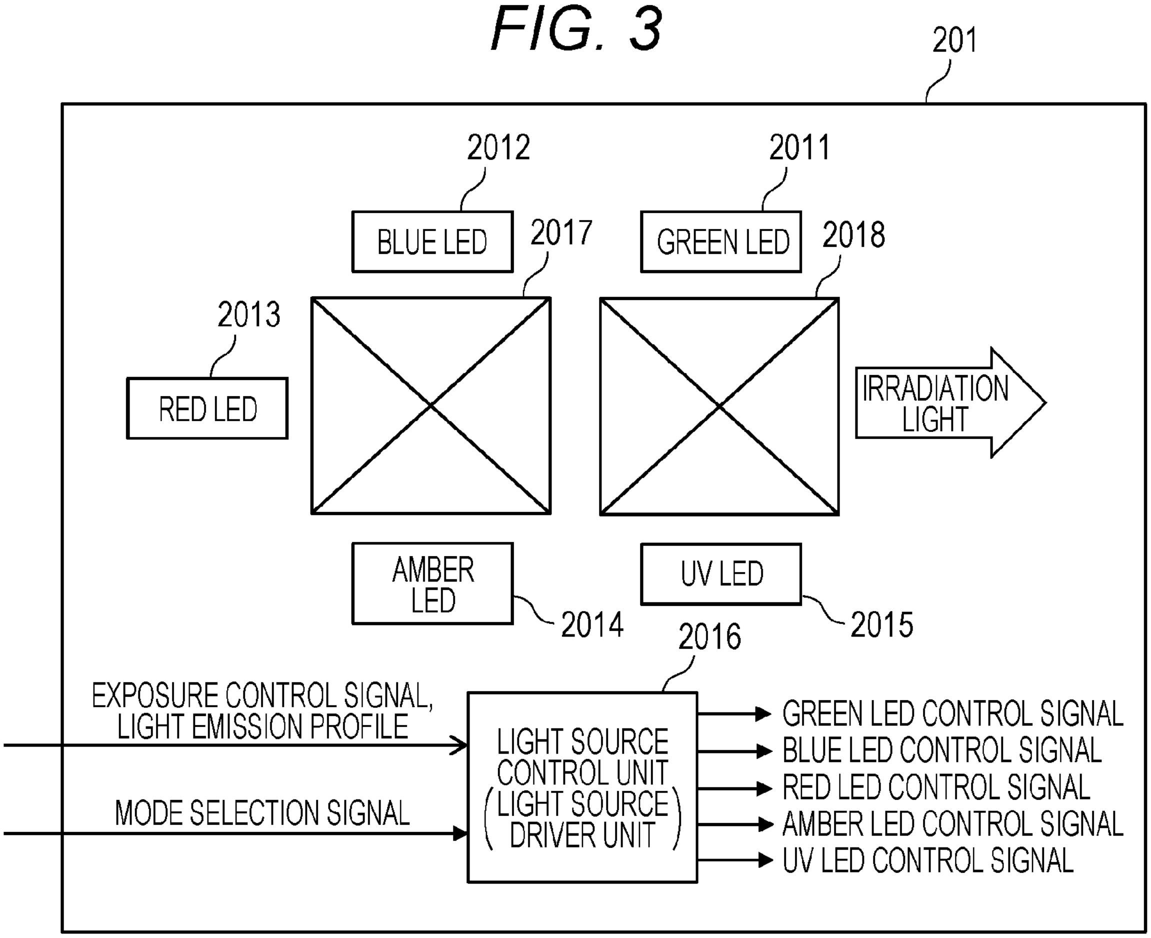
FIG. 3 is a diagram illustrating an internal configuration example of a light source device 201 provided inside a processor 200.

FIG. 3 is a diagram illustrating an internal configuration example of the light source device 201 provided inside the processor 200, for example.

The light source device 201 includes the green LED 2011 that emits green light, the blue LED 2012 that emits blue light, the red LED 2013 that emits red light, the amber LED 2014 that emits amber light, the UV LED 2015 that emits UV light, the light source control unit 2016 that controls the light emission of the respective LEDs 2011 to 2015, and cross prisms 2017 and 2018.

When receiving the exposure control signal from the system controller 202, the light source control unit 2016 changes a light emission profile of the respective LEDs and performs exposure adjustment (light amount adjustment) by controlling a light emission period and an applied current value of each LED that is currently emitting light (the combination of LEDs to emit light is determined depending on the observation mode) (see FIGS. 11 and 13 to be described later). For example, after changing the light emission profile by one step, the light source control unit 2016 determines whether to change the light emission profile again and perform the exposure adjustment on the basis of the exposure control signal determined by a photometry result (the comparison result with the correct luminance value) by the photometric unit 203.

In addition, the light source control unit 2016 determines the combination of LEDs to emit light on the basis of the mode selection signal indicating the observation mode selected by the operator. At the start of the light emission, the light source control unit 2016 controls the light emission of the respective LEDs on the basis of, for example, a predetermined light emission profile (a default light emission period and a default drive current value), and thereafter, performs the exposure adjustment as described above.

<Each LED Light Source>

Figure 4:
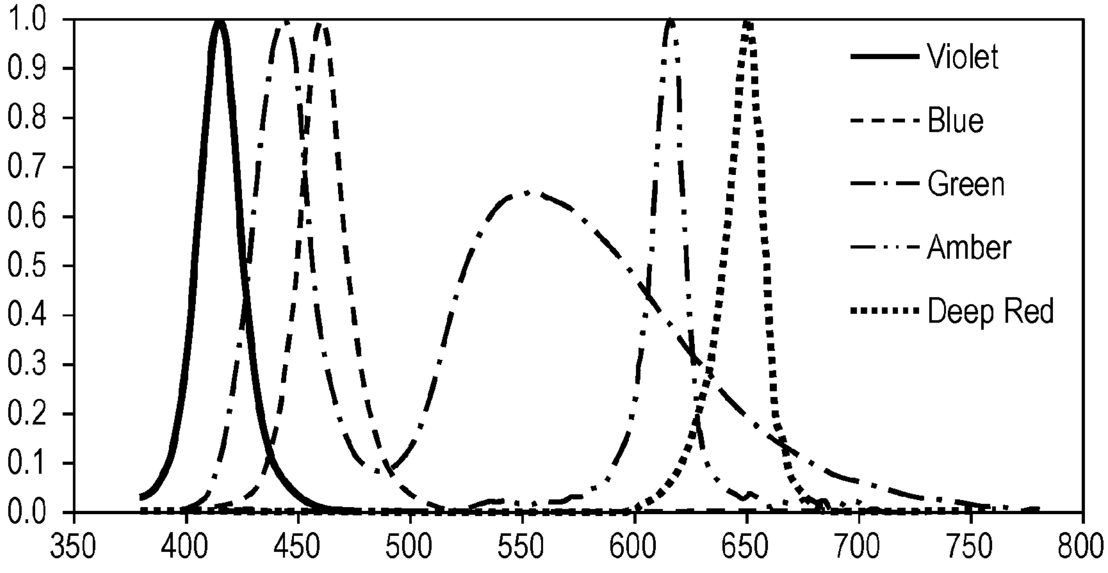
FIG. 4 is a diagram illustrating the spectra (wavelength characteristics) of respective LEDs 2011 to 2015.

FIG. 4 is a diagram illustrating the spectra (wavelength characteristics) of the respective LEDs 2011 to 2015. In addition, FIG. 5 is a diagram illustrating the characteristics of illumination light (light illuminating the observation site) generated by transmitting the respective LEDs through the cross prisms 2017 and 2018.

The green LED 2011 has a transmission wavelength band of 540 nm to 575 nm, a peak wavelength of 550 nm, and a half-value width of 30 nm. A phosphor is mounted on the green LED 2011, and the phosphor emits light in a transmission wavelength band of about 400 nm to 780 nm as illustrated in FIG. 4. That is, although substantially white light is emitted by the green LED and the phosphor, this white light is an intermediate product. As described later, the transmission wavelength band is narrowed by the cross prism 2018, and the observation site is irradiated with green light. The blue LED 2012 has a transmission wavelength band of 460 nm to 490 nm, a peak wavelength of 456 nm, and a half-value width of 21 nm. The red LED 2013 has a transmission wavelength band of 630 nm to 1000 nm, a peak wavelength of 650 nm, and a half-value width of 20 nm. The amber LED 2014 has a transmission wavelength band of 600 nm to 615 nm, a peak wavelength of 613 nm, and a half-value width of 19 nm. The UV LED 2015 has a transmission wavelength band of 385 nm to 425 nm, a peak wavelength of 405 nm, and a half-value width of 14 nm.

Figure 5:
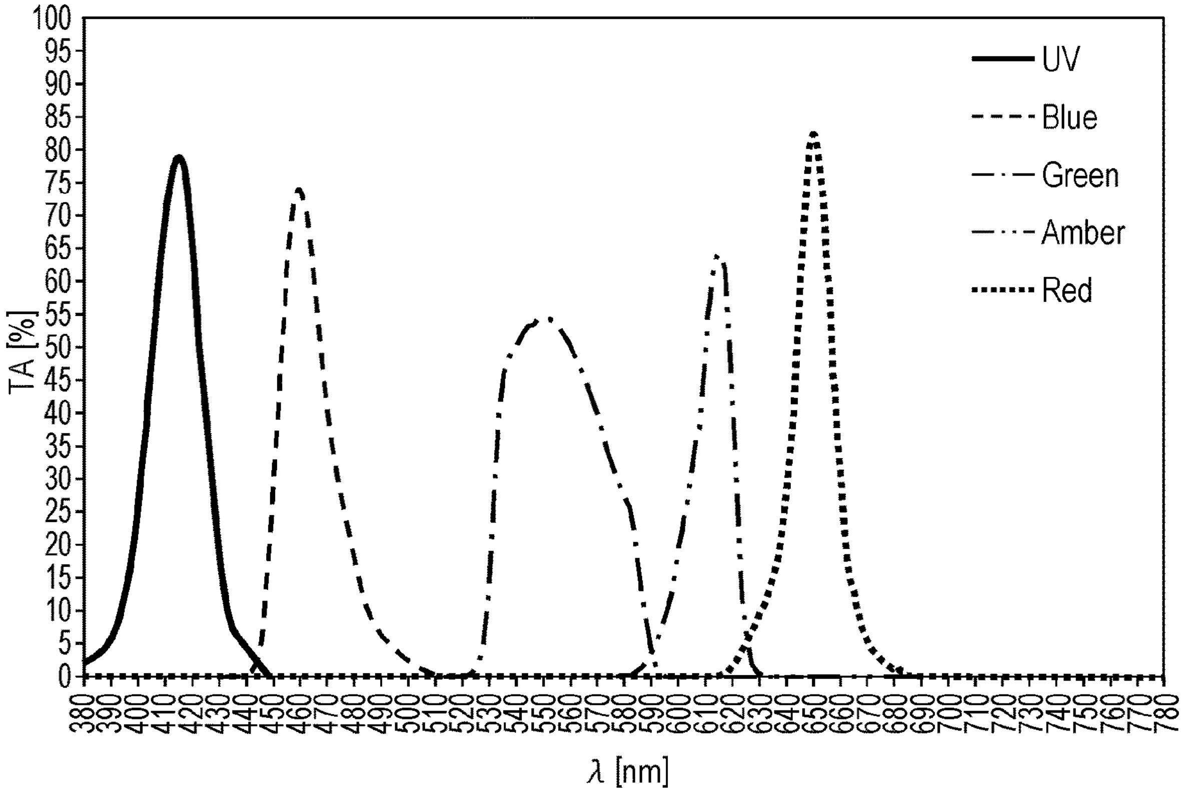
FIG. 5 is a diagram illustrating the characteristics of illumination light (light illuminating an observation site) generated by transmitting the respective LEDs through cross prisms 2017 and 2018.

Each light (the white light as the intermediate product, the blue light, the red light, the amber light, and the UV light) emitted from each of the LEDs 2011 2015 including the green LED 2011 on which the phosphor is mounted is transmitted through the cross prisms 2017 and 2018 to become each light having the characteristics illustrated in FIG. 5, and is applied to the observation site. Specifically, the transmission wavelength band of the white light emitted from the green LED 2011+the phosphor is limited by the cross prism 2018, so that the white light becomes green light of 520 nm to 595 nm. The blue light emitted from the blue LED 2012 becomes blue light of 440 nm to 500 nm by the cross prisms 2017 and 2018. In addition, the red light emitted from the red LED 2013 becomes red light of 620 nm to 630 nm by the cross prisms 2017 and 2018. The amber light emitted from the amber LED 2014 becomes amber light of 580 nm to 630 nm by the cross prisms 2017 and 2018. Furthermore, the UV light emitted from the UV LED 2015 becomes UV light of 380 nm to 450 nm by the cross prism 2018.

<Correction of Linearity Difference of Each LED>

Figure 6:
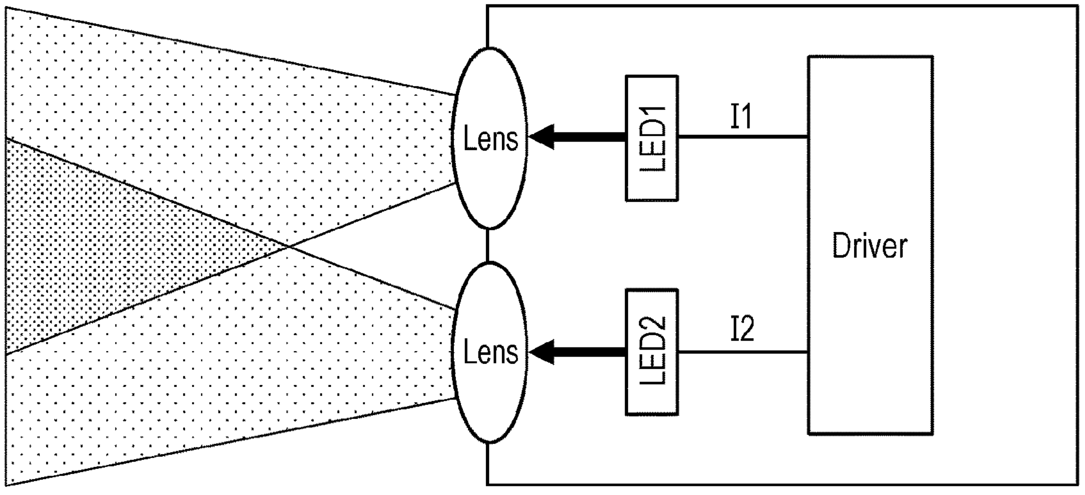
FIG. 6 is a diagram illustrating a configuration example of a light source using LEDs having different light distributions.

In a case where the light source device 201 includes the plurality of LEDs, not only the wavelengths of the light beams emitted from the LEDs 2011 to 2015 but also their light distributions (light intensity distributions in each direction) are different (see FIG. 6: a configuration example of a light source using LEDs having different wavelengths) in some cases. There may be a change in the color or light distribution of the emitted light from the respective LEDs 2011 to 2015. In addition, in some types of LEDs, when a forward voltage is lowered in order to lower the drive current value, the drive current value rapidly drops and the LED does not emit light. Thus, the drive current value cannot be greatly lowered in some cases. In order to cope with such a situation, it is necessary to dynamically correct a difference in linearity of an emitted light amount/electric current ratio of each of the LEDs 2011 to 2015 in accordance with the drive current control of each of the LEDs 2011 to 2015.

Figure 7:
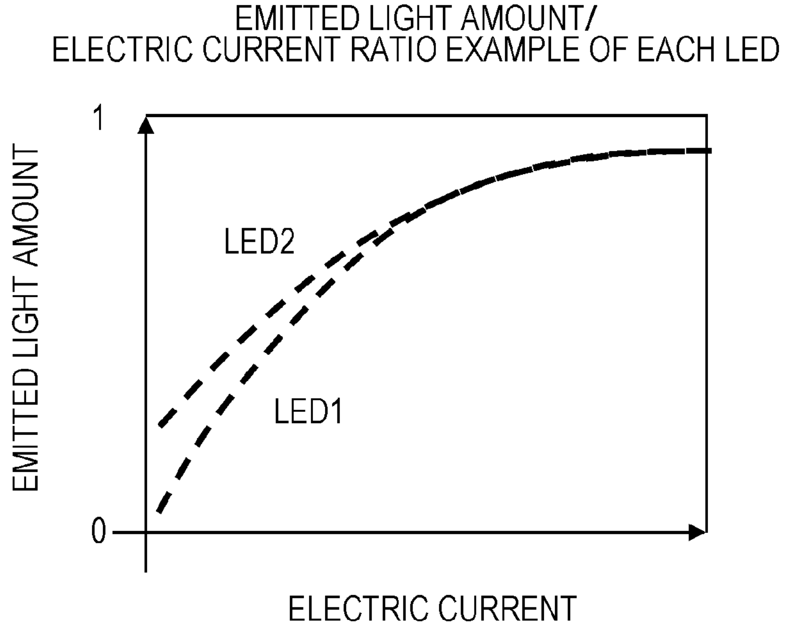
FIG. 7 is a diagram illustrating a graph of an emitted light amount/electric current ratio of each LED.

However, since the process of dynamically correcting the difference in linearity is complicated, it is preferable to determine the drive current value in advance so that there is no difference in linearity. Therefore, in the present embodiment, a correction table for correcting the linearity of the emitted light amount/electric current ratio is prepared in advance, and the drive current values of the respective LEDs 2011 to 2015 are determined using the correction table. FIG. 7 is a diagram illustrating a graph of the emitted light amount/electric current ratio of each LED. Although FIG. 7 illustrates a relationship between only two LEDs (an LED 1 and an LED 2) as an example, the same applies to the case of using the five LEDs 2011 to 2015 as described in the present embodiment. The relationship between the emitted light amount/electric current ratios of the respective LEDs as illustrated in FIG. 7 can be acquired by measuring the LEDs in advance. Therefore, the correction table having the reciprocal of the relationship between the emitted light amount/electric current ratios as a correction parameter is provided in advance (stored in a memory) as a correction value, and the light source control unit 2016 calculates the corrected drive current value by multiplying the drive current value by the correction parameter corresponding to a desired emitted light amount (a target emitted light amount obtained by the exposure adjustment), and drives each LED. This makes it possible to appropriately control the linearity of the emitted light amount/electric current ratio even in a case where the wavelengths and the light distributions of the emitted light beams of the respective LEDs are different.

<Configuration Example of Imaging Surface of Image Sensor>

Figure 8:
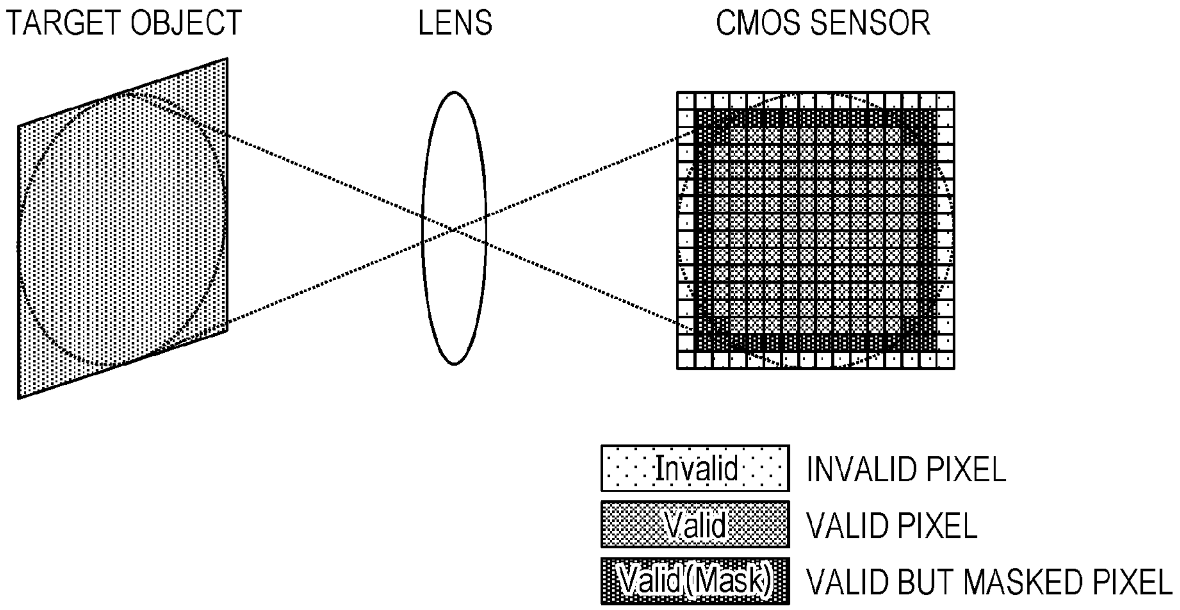
FIG. 8 is a diagram illustrating a valid pixel area and an invalid area of a rolling shutter type image sensor using a CMOS sensor as an example.

FIG. 8 is a diagram illustrating a valid pixel area and an invalid area of a rolling shutter type image sensor using a CMOS sensor as an example. The CMOS sensor includes the valid pixel area that can be imaged and the invalid area that cannot be imaged. In addition, a part (peripheral portion) of the valid pixel area is masked to be an area where it is substantially not possible to acquire an image signal. In a case of capturing an image using such an image sensor (in a case of global exposure), various phenomena (features) appear in the captured image. In the present embodiment, a period during which the image is not displayed on a screen is a global exposure period, but the idea of the present embodiment is not limited to this case.

<Typical Light Adjustment Control Process>

Figure 9:
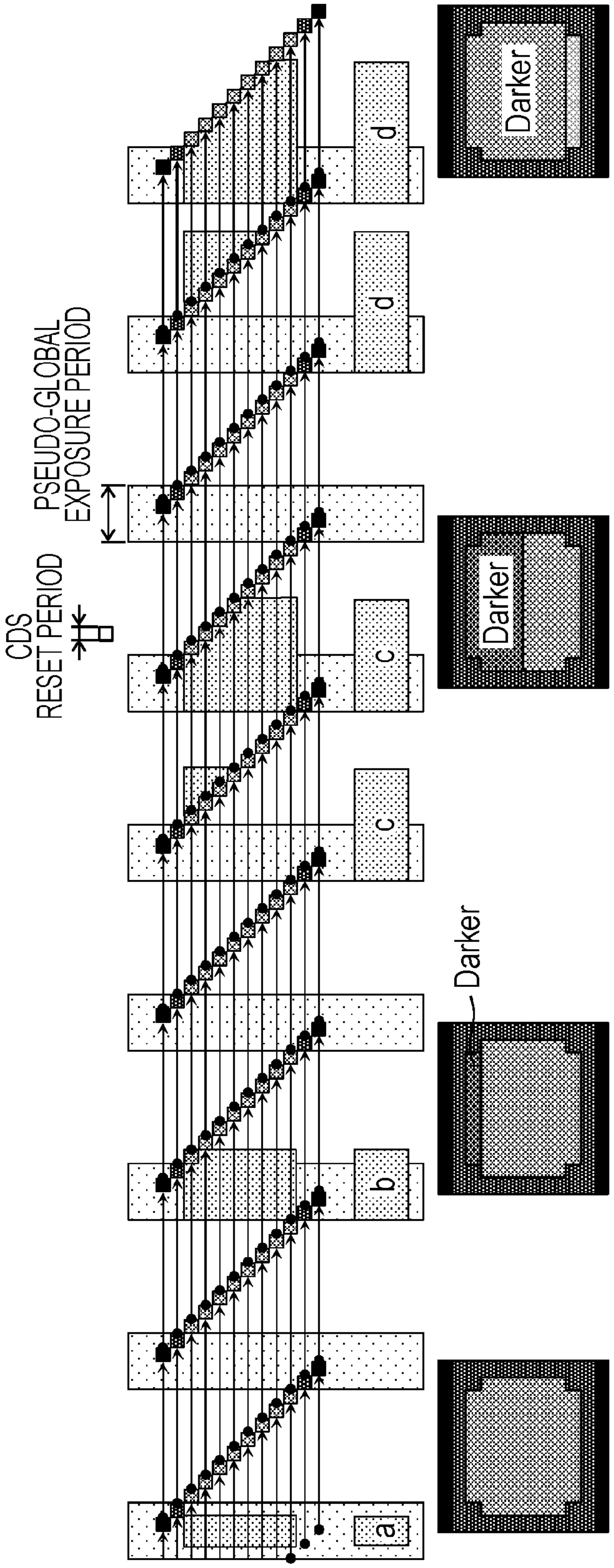
FIG. 9 is a diagram illustrating a phenomenon (feature) appearing in an image captured using the image sensor having an imaging surface illustrated in FIG. 8 in a case where a typical light adjustment control process is executed.

FIG. 9 is a diagram illustrating a phenomenon (feature) appearing in the image captured using the image sensor having an imaging surface illustrated in FIG. 8 in a case where a typical light adjustment control process is executed. When pulsed light emission is performed within a readout period of a line not shown on the screen as illustrated in FIG. 9*a*, pseudo-global exposure can be achieved. In addition, when the pulsed light emission is performed as illustrated in FIG. 9*b*, the exposure amount of the uppermost line of the valid pixel area is smaller than those of other lines by a period from readout to reset, and the uppermost line appears somewhat darker. However, when the period from readout to reset is sufficiently shorter than a pseudo-global exposure period (for example, less than 1%), the darkness is not noticeable. Furthermore, when the pulsed light emission is performed as illustrated in FIG. 9*c*, about the upper half of the valid pixel area becomes slightly dark, but the darkness of the area becomes further unnoticeable as the total exposure amount of the respective lines increases. As described above, as the pulsed light emission period becomes longer, the area having a different exposure amount becomes wider, but the difference in brightness due to the different exposure amount becomes unnoticeable. Furthermore, when the pulsed light emission period is further extended as illustrated in FIG. 9*d*, the ratio smoothly changes from the lower part to the upper part of the screen along with an increase in immediately preceding pulse component. For this reason, artifacts and distortions (unfavorable phenomena) become less noticeable.

Figure 10:
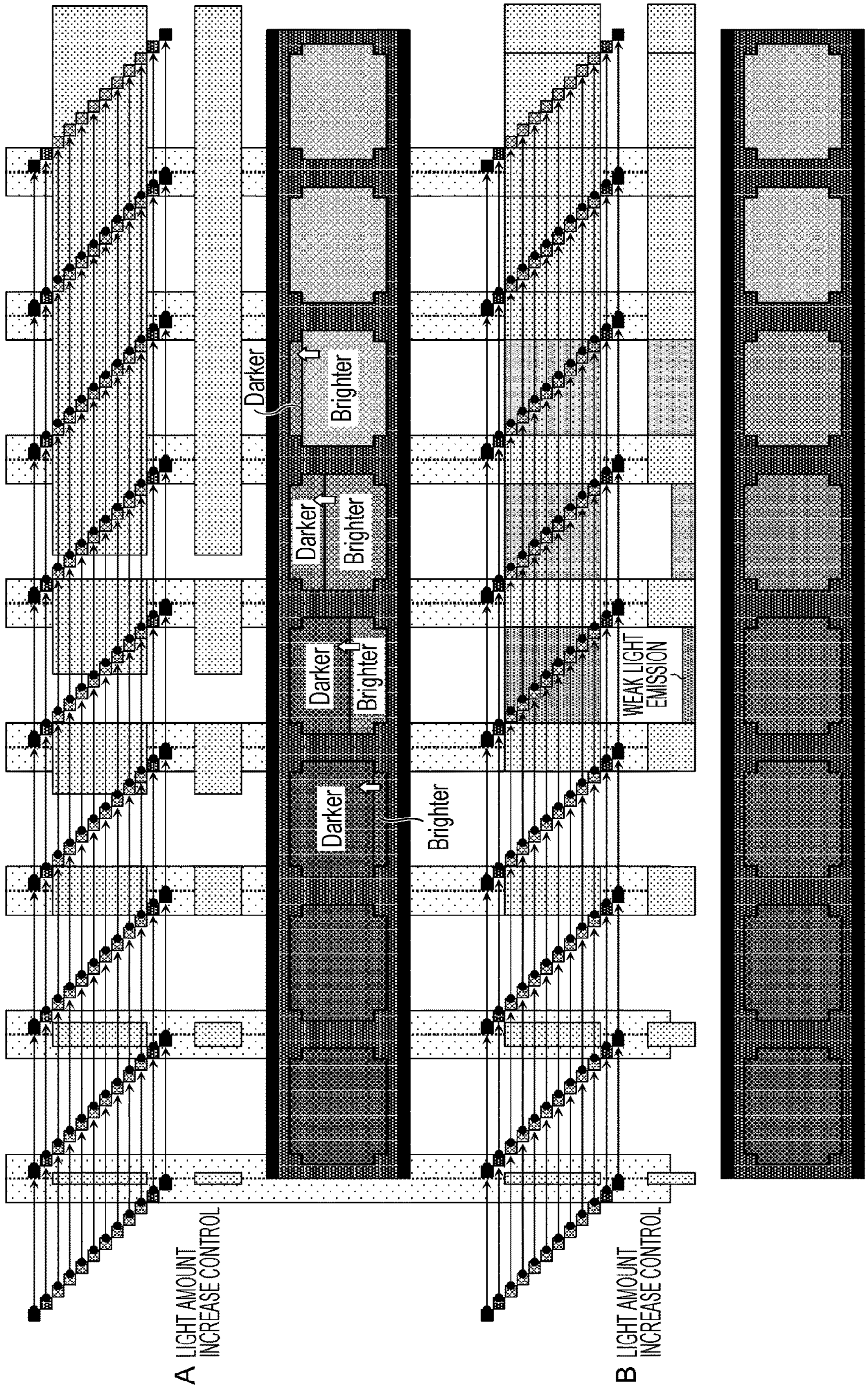
FIG. 10 is a diagram illustrating an operation in a case of performing extension control (only time control) of a pulsed light emission period, and the state of an acquired image corresponding to the operation.

FIG. 10 is a diagram illustrating an operation in a case of performing the extension control (only time control) of the pulsed light emission period, and the state of an acquired image corresponding thereto. FIG. 10 is a diagram illustrating the above-described effect of extending the pulsed light emission period in more detail. As illustrated in FIG. 10A, when the pulsed light emission period is changed between adjacent frames, a difference in exposure amount between lines to be read out before and after a pulse end increases, so that a phenomenon occurs in which a horizontal stripe appears to move up and down on the image. On the other hand, as illustrated in FIG. 10B, when a weak light emission intensity is changed between the adjacent frames, the horizontal stripe on the image becomes unnoticeable.

However, it is not sufficient to simply extend the exposure period as in FIGS. 9 and 10. This is because when the exposure amount increases, an overexposure phenomenon (a bright portion becomes blank in the image) may occur in the image depending on a surrounding environment of the observation site. Therefore, it is necessary to avoid the occurrence of distortions and artifacts while maintaining a correct exposure amount (with which the image is not too dark and the overexposure is not caused).

<Improved Light Adjustment Control Process>

Figure 11:
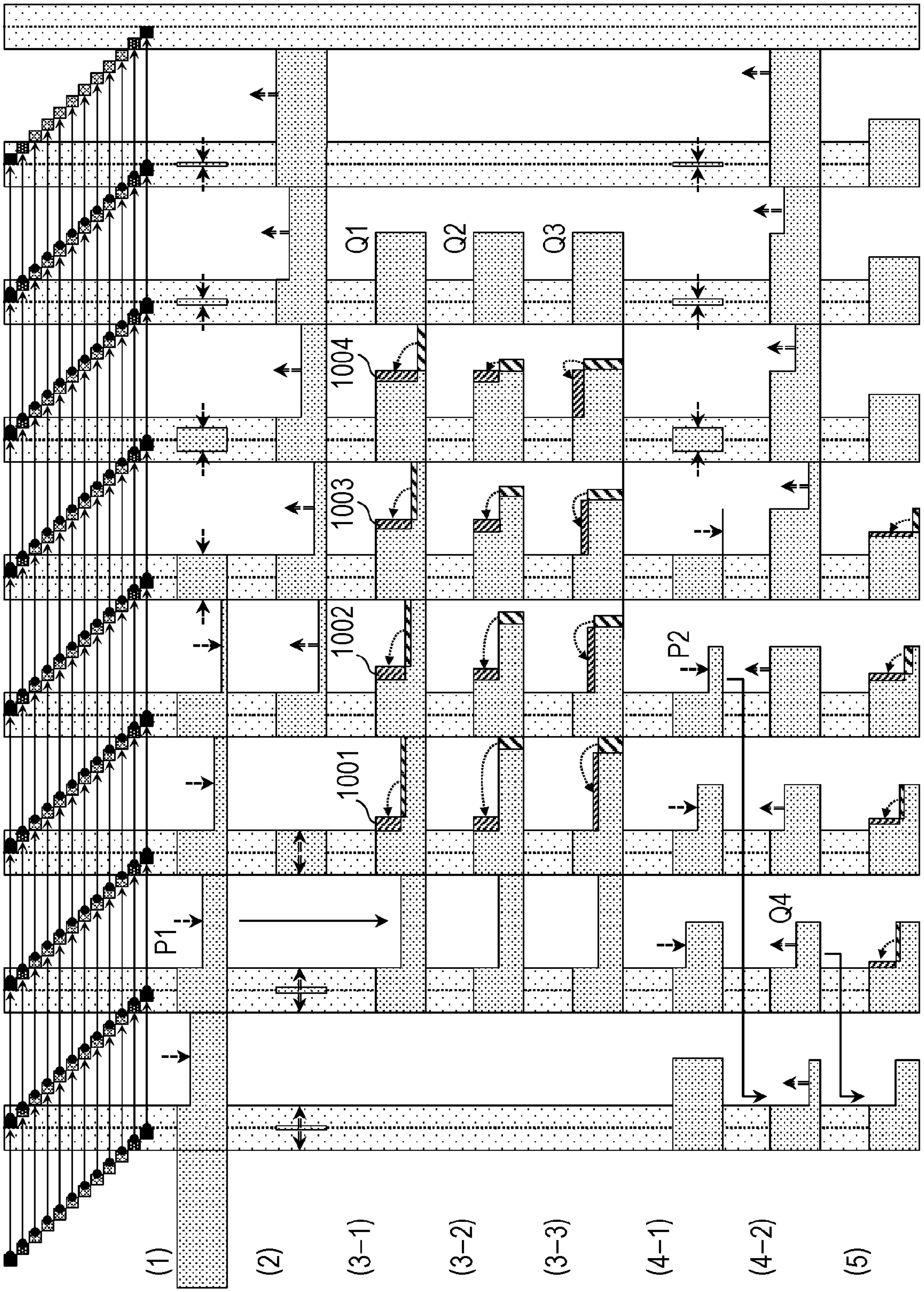
FIG. 11 is a diagram illustrating the outline of an improved light adjustment control process according to the present embodiment.
Figure 12:
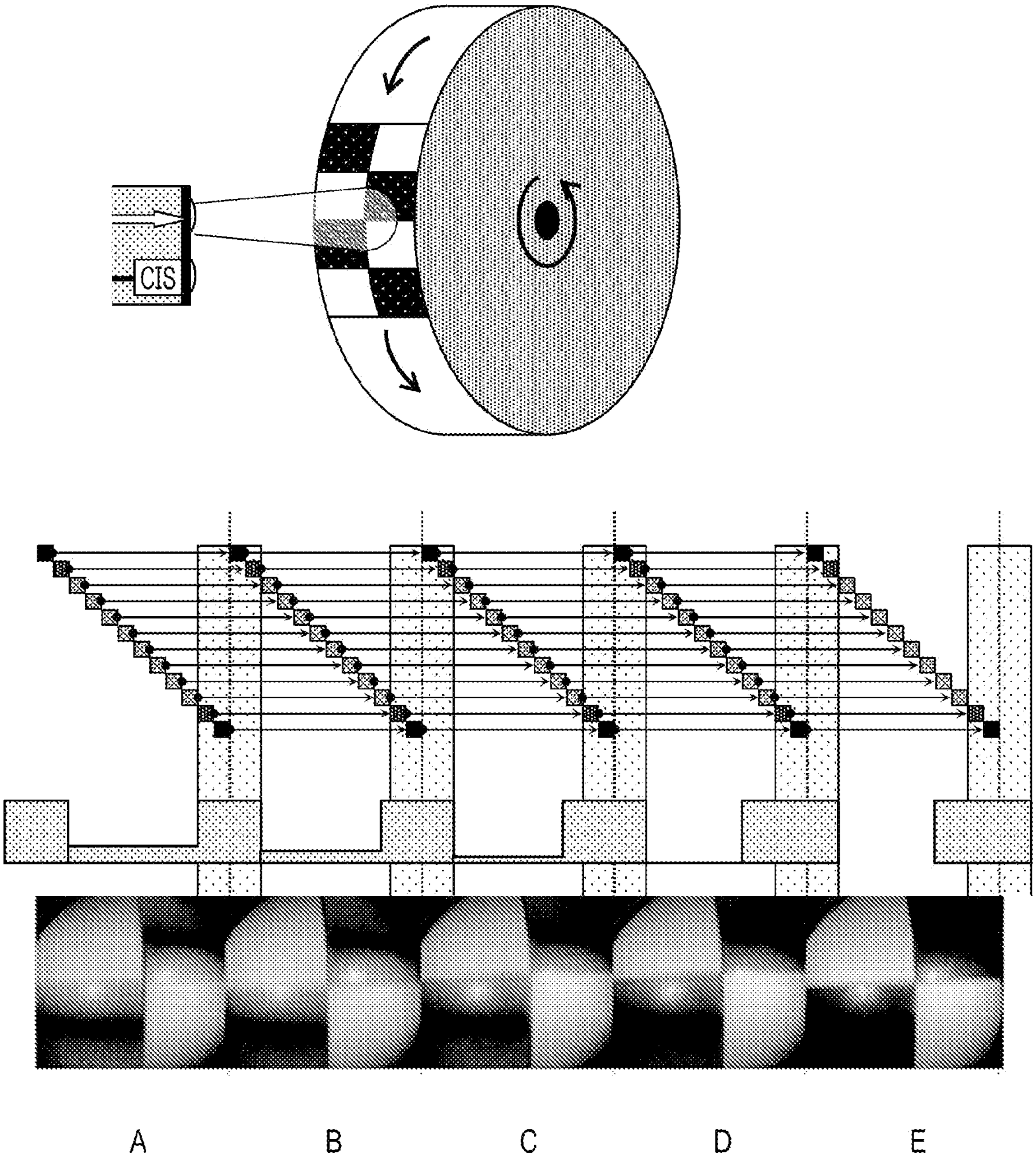
FIG. 12 is a diagram for explaining the influence of an intensity difference between strong light emission and weak light emission.

FIG. 11 is a diagram illustrating the outline of an improved light adjustment control process according to the present embodiment. In addition, FIG. 12 is a diagram for explaining the influence of an intensity difference between strong light emission and weak light emission.

In a case where light adjustment control is performed by controlling the light emission operation of the light source so that the intensity of light (strong light emission) in the pseudo-global exposure period is equal to or higher than the intensity of light (weak light emission) in a rolling shutter period, and raising or lowering the weak light emission intensity, it is typical to perform the light adjustment control by changing the strong light emission intensity or a strong light emission period within the range of the pseudo-global exposure period when the weak light emission in the rolling shutter period is equal to or lower than a predetermined threshold value.

However, as illustrated in FIG. 12A, in a case where the intensity difference between the strong light emission and the weak light emission is large, and the ratio (integral value ratio) of "the product of the intensity and the period of the strong light emission (strong light emission integral value)" to "the product of the intensity and the period of the weak light emission (weak light emission integral value)" is not sufficiently large, an unnatural image generated as if by double exposure of a short-time exposure image and a long-time exposure image is observed. Particularly for a moving object, this phenomenon tends to give a sense of discomfort to the operator. In addition, in a case where the light source includes the plurality of LEDs having different wavelengths or different light distributions (in the case of the present embodiment), the color or light distribution of the emitted light changes unless the emitted light amounts of the respective LEDs are set to a fixed ratio. Therefore, as described above, in order to control the drive current value in a case where there is a variation in the linearity of the light emission amount/electric current ratio of each LED, it is necessary to correct the difference in the linearity of the light emission amount/electric current ratio of each LED, and the process becomes complicated.

Therefore, to reduce the complication of the process, any of the following processes 1 to 3 is executed in a case where the weak light emission intensity is lower than a predetermined threshold value, in addition to the process of correcting the linearity of the emitted light amount/electric current ratio of each LED by the above-described correction table.

Process 1: Process of extending the strong light emission period while lowering the weak light emission intensity Process 2: Process of extending the strong light emission period while shortening the weak light emission period Process 3: Process of raising the weak light emission intensity while shortening the weak light emission period That is, in all of the process 1 to the process 3, the weak light emission is sequentially converted into the strong light emission (restoration control process) by taking time so as not to cause a change in brightness of the observation screen, the phenomenon in which the horizontal stripe moves up and down in the image, and a brightness decrease (decrease in brightness) of the screen while keeping the same total light emission integral value (the strong light emission integral value+the weak light emission integral value) before and after the process. By any of these processes, it is possible to eliminate the troubles in which the unnatural image as if by the double exposure is formed with the lapse of time and the color or light distribution of the emitted light changes. For example, it is possible to change the state of FIG. 12A (an image in which the double exposure is performed and the horizontal stripe appears) to the state of FIG. 12E (an image in which the double exposure and the brightness/color unevenness are eliminated, and no horizontal stripe appears).

The processes 1 to 3 will be specifically described with reference to FIG. 11. First, the light source control unit 2016 performs the light adjustment control on the respective LEDs 2011 to 2015 until the exposure comes to have a correct level by setting the pseudo-global exposure period to the strong light emission and the rolling shutter period to the weak light emission. As illustrated in FIG. 11(1), in a case where the light emission intensity is lowered from a state in which light is emitted with a uniform intensity for the entire period (the pseudo-global exposure period and the rolling shutter period), the light adjustment control is executed such that the light emission intensity in the rolling shutter period (weak light emission period) is lowered, and when the rolling shutter period reaches a non-light emission state, the pseudo-global exposure period is shortened, or the light emission intensity in the pseudo-global exposure period is lowered. On the other hand, as illustrated in FIG. 11(2), in a case where the light emission intensity is raised, the light adjustment control is executed such that the light emission period in the pseudo-global exposure period is extended, or the light emission intensity in the pseudo-global exposure period is raised, and when the light emission period and the light emission intensity are maximized in the pseudo-global exposure period, the light emission intensity in the rolling shutter period (weak light emission period) is sequentially raised.

For example, suppose that a correct exposure level (for example, a predetermined correct level $\pm\alpha$: $\alpha$ is a margin) is reached in a light emission pattern P1 by the light adjustment control of FIG. 11(1). In a case of performing imaging while keeping this state, the image as if by the double exposure illustrated in FIG. 12A is generated. This is because images with different levels of brightness are obtained from an image by the strong light emission and an image by the weak light emission, and these images overlap with each other. Therefore, the light adjustment control process is shifted to any of FIG. 11(3-1) to FIG. 11(3-3) while the exposure level of the light emission pattern P1 is being maintained. Here, FIG. 11(3-1) corresponds to the above process 1, FIG. 11(3-2) corresponds to the above process 2, and FIG. 11(3-3) corresponds to the above process 3. In the process 1 to the process 3, in a case where the weak light emission intensity is equal to or lower than the predetermined threshold value, the process of converting the weak light emission intensity into the strong light emission period little by little in each frame is performed. As a result, it is possible to eliminate the weak light emission period without generating the horizontal stripe in the captured image, and to avoid the generation of the unnatural image and the change in the color and light distribution of the light from each light source.

More specifically, in the process 1 (FIG. 11(3-1)), the value (weak light emission area) of the light emission intensity×the light emission period in the weak light emission is gradually converted into the strong light emission period so that the total area (total light emission integral value) of the strong light emission period and the weak light emission period remains the same, and the light adjustment control is executed by a light emission pattern Q1 (restoration process). For example, in the light emission of restored portions 1001 to 1004 in FIG. 11, an area below the uppermost line of the valid pixel area (see FIG. 8) of the image sensor (CMOS sensor) is exposed in a frame in which the corresponding restoration process is executed. Therefore, in this frame, an image portion corresponding to the uppermost line becomes dark, but in the next frame, an image signal corresponding to the uppermost line can be acquired.

In the process 2 (FIG. 11(3-2)) and the process 3 (FIG. 11(3-3)), a light adjustment control process according to a mode (example) different from the process 1 is performed. That is, similarly to the process 1, the process 2 and the process 3 are performed by gradually converting the value (weak light emission area) of the light emission intensity× the light emission period in the weak light emission into the strong light emission period so that the total area (total light emission integral value) of the strong light emission period and the weak light emission period remains the same (restoration process). In the process 2, the strong light emission period is extended by shortening the weak light emission period while maintaining the weak light emission level constant, and gradually assigning a light emission integral value corresponding to the weak light emission area decreased by shortening the period, to the strong light emission period. In addition, in the process 3, the strong light emission period is extended by shortening the weak light emission period, and assigning a light emission integral value corresponding to the weak light emission area decreased by shortening the period, to the weak light emission, to gradually raise the weak light emission intensity. Light emission patterns Q1 to Q3 are executed by the processes 1 to 3. Note that the light emission patterns Q1 to Q3 are all the same pattern.

When the change in the light emission by the light adjustment control in any of the process 1 to the process 3 (FIG. 11(3-1) to FIG. 11(3-3)) is executed sufficiently slowly, it is possible to avoid the generation of the unnatural image as if by the double exposure without giving a sense of discomfort to the operator. For example, in a state where the light adjustment control by the light emission patterns Q1 to Q3 is executed, the image as illustrated in FIG. 12E is obtained, in which the double exposure is eliminated.

In a case where the exposure level increases to become too bright (the exposure level deviates from the correct value) due to an object moving (including camera movement: relatively moving) during irradiation with light from each light source in the light emission patterns Q1 to Q3, the correct exposure level is searched by a process illustrated in FIG. 11(4-1). For example, in a case where it is determined that the exposure level is correct at the time of a light emission profile P2 (when the exposure level that is too bright becomes correct: whether the exposure level is correct is determined by the photometry result by the photometric unit 203 similarly to the above description), the restoration process (any of the processes 1 to 3) is executed from the state of the light emission profile P2, and the weak light emission portion is restored to the strong light emission. On the other hand, in a case where the exposure level decreases to become too dark (the exposure level deviates from the correct value) due to the object moving (including the camera movement: relatively moving) during light emission in the state of the light emission profile P2, the exposure level is corrected to the correct level by a process illustrated in FIG. 11(4-2) (the process of raising the weak light emission level illustrated in FIG. 11(4-2) is sequentially executed until the exposure level reaches the correct level). For example, in a case where the exposure level reaches the correct level with a light emission profile Q4, the restoration process of any of the process 1 to the process 3 is executed from the state of the exposure level of the light emission profile Q4 as illustrated in FIG. 11(5).

<Details of Light Adjustment Control Process and Response to Sharp Movement of Endoscope>

Figure 13:
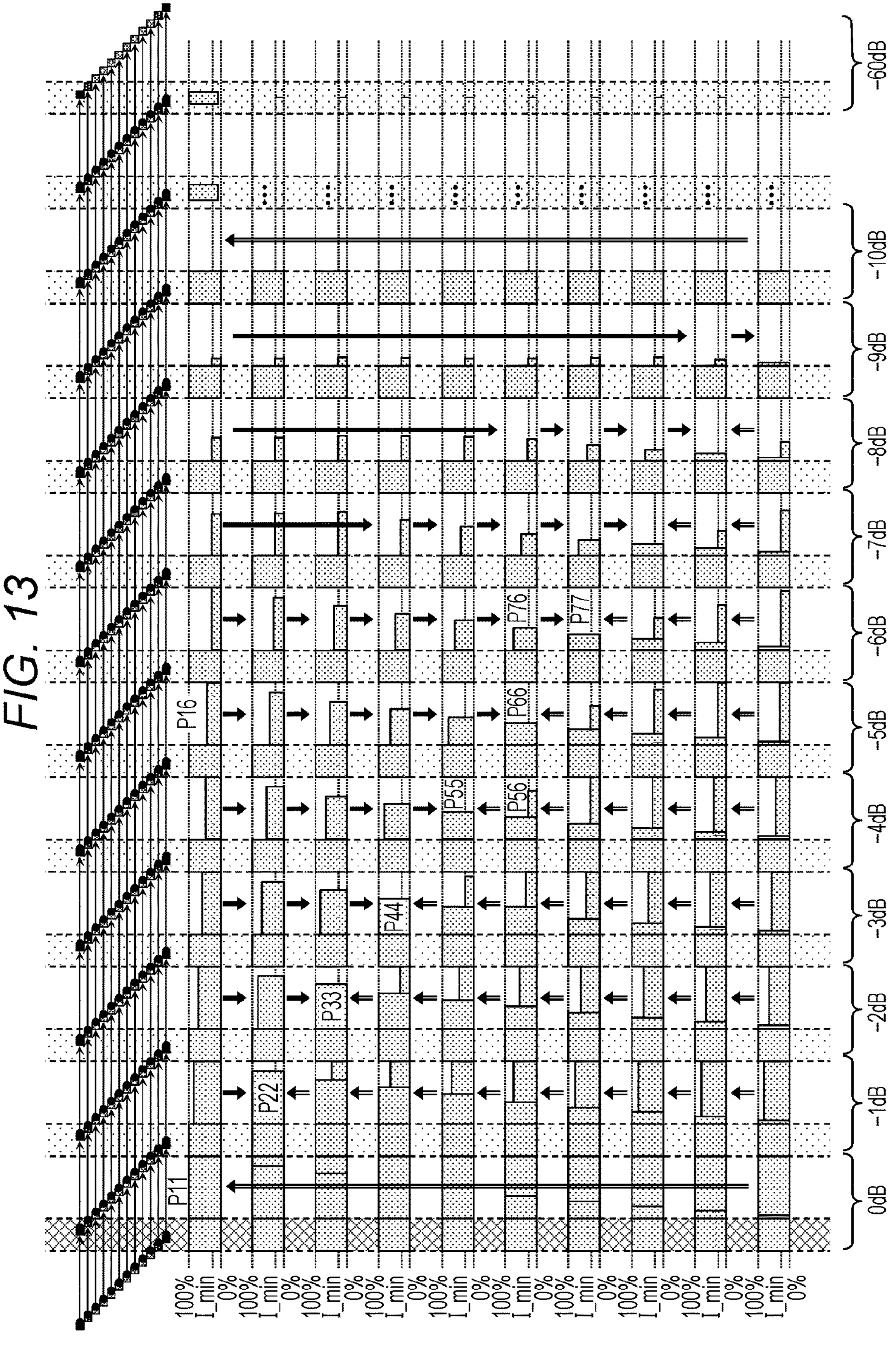
FIG. 13 is a diagram illustrating the light adjustment control process of FIG. 11 in more detail, and is a diagram for explaining an inappropriate example of the light adjustment control process.

FIG. 13 is a diagram illustrating the light adjustment control process of FIG. 11 in more detail, and is a diagram for explaining an inappropriate example of the light adjustment control process.

In FIG. 13, in a case where it is determined that the image is overexposed (the exposure level of a light emission profile P11 is not correct) when, for example, the object is irradiated with light of a light emission profile P11, the weak light emission intensity in the rolling shutter period is sequentially lowered (sequentially shifted from the profile P11 to the right profile). Here, suppose that, for example, the correct exposure level (the exposure level at which the overexposure disappears and the image is easy to view) is obtained with a light emission profile P16. Subsequently, the above-described restoration process (any of the process 1 to the process 3) is executed, and the weak light emission period is converted into the strong light emission period. As a result, the captured image is changed from the state of FIG. 12A (when the object is irradiated with the light emission profile P16, the unnatural image as if by the double exposure is obtained) to the state of FIG. 12E, and the phenomena such as the overexposure and the double exposure are also eliminated. When there is no change in the brightness of the captured image (when the change falls within a predetermined threshold value), the light emission from the respective light sources 2011 to 2015 is performed with a light emission profile P66.

In FIG. 13, the light adjustment control is performed such that the light emission profile is sequentially shifted rightward from the light emission profile P11 to the light emission profile P16, and continues to be shifted to the light emission profile P66 by the restoration process. However, other paths (for example, a path shifted while moving so as to proceed obliquely (but moving only slowly in the upper/lower direction) as indicated by P11→P12→P13→P24→P25→P36→P46→P56→P66), that is, while moving so as to simultaneously perform the light adjustment control and the restoration process) may be adopted. However, the light adjustment control process cannot be executed along the path of the light emission profiles P11→P22→P33→P44→P55→P66. This is because simply time-controlling the strong light emission period causes a phenomenon in which a bright portion of the image moves up and down (horizontal stripe movement decrease) as illustrated in FIG. 10A. In order not to cause this phenomenon, it is necessary to slowly restore the intensity distribution of the weak light emission to the strong light emission (restoration process).

For example, in a case where it is necessary to further increase the brightness from the state of the light emission profile P66 in FIG. 13, when the intensity distribution of the strong light emission is extended in the time direction, the above-described horizontal stripe movement phenomenon is caused. Thus, the intensity level of the weak light emission is raised first. For example, the light adjustment control is performed such that the light emission profile is shifted from the light emission profile P66 to a light emission profile P56, and then to a light emission profile P55. However, rapidly shifting the light emission profile in the upper/lower direction is equivalent to rapidly shifting the profile in the time direction. Thus, it is important to execute the restoration process in the vertical direction after adjusting the exposure level to the correct level by moving the profile in the horizontal direction with respect to sharp movement of the endoscope (image sensor).

On the other hand, when it is necessary to decrease the brightness from the state of the light emission profile P66, it is not possible to immediately shift the light emission profile P66 to a light emission profile P77. Therefore, a process is executed in which the strong light emission level in the rolling shutter period is temporarily lowered to the state of a light emission profile P76 as the weak light emission period, and thereafter the state of the light emission profile P77 is obtained by the restoration process.

After the correct exposure level is determined, the light adjustment control process is executed up to the light emission profile (Pkk; k=1, 2, . . . , n: n is an integer of 1 or more) where the up arrow and the down arrow meet.

In addition, in FIG. 13, an electric current value Imin indicates a correction limit of the linearity of the emitted light amount/electric current ratio of each light source described above, or an electric current value at which each LED is turned off. Therefore, in the present embodiment, in a case where the light adjustment control for lowering the light emission intensity of the weak light emission is executed, the brightness is adjusted by shortening the light emission period, instead of lowering the light emission intensity, after lowering the light emission intensity to Imin. In this case, when Imin is sufficiently smaller than the strong light emission intensity×time, the horizontal stripe is not visible.

<Offset Light Emission Process>

Figure 14:
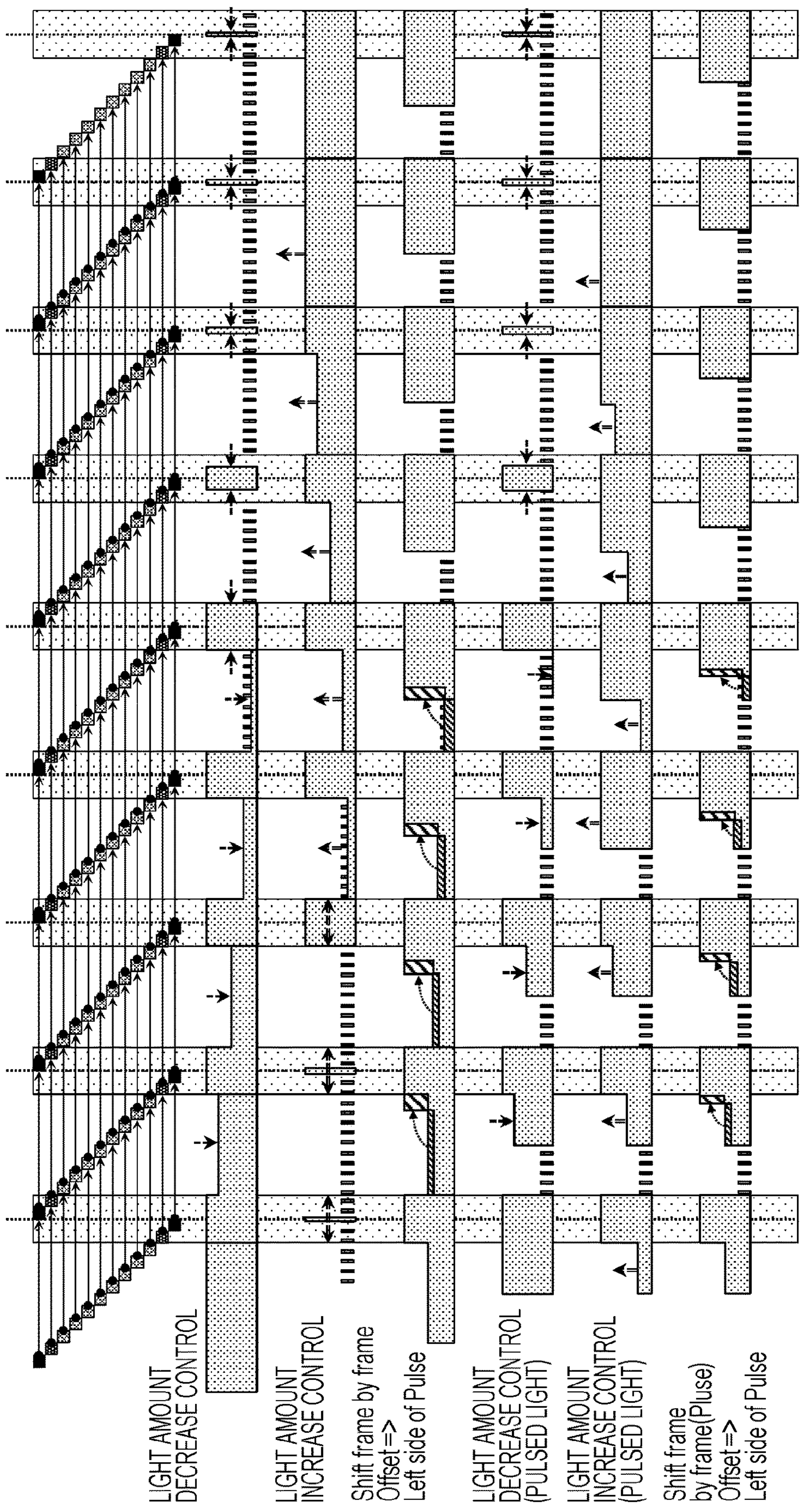
FIG. 14 is a diagram for explaining an offset light emission process (faint pulses) in a non-light emission period (alternatively, a weak light emission period in which a light emission intensity is so weak that light emission cannot be visually recognized).
Figure 15:
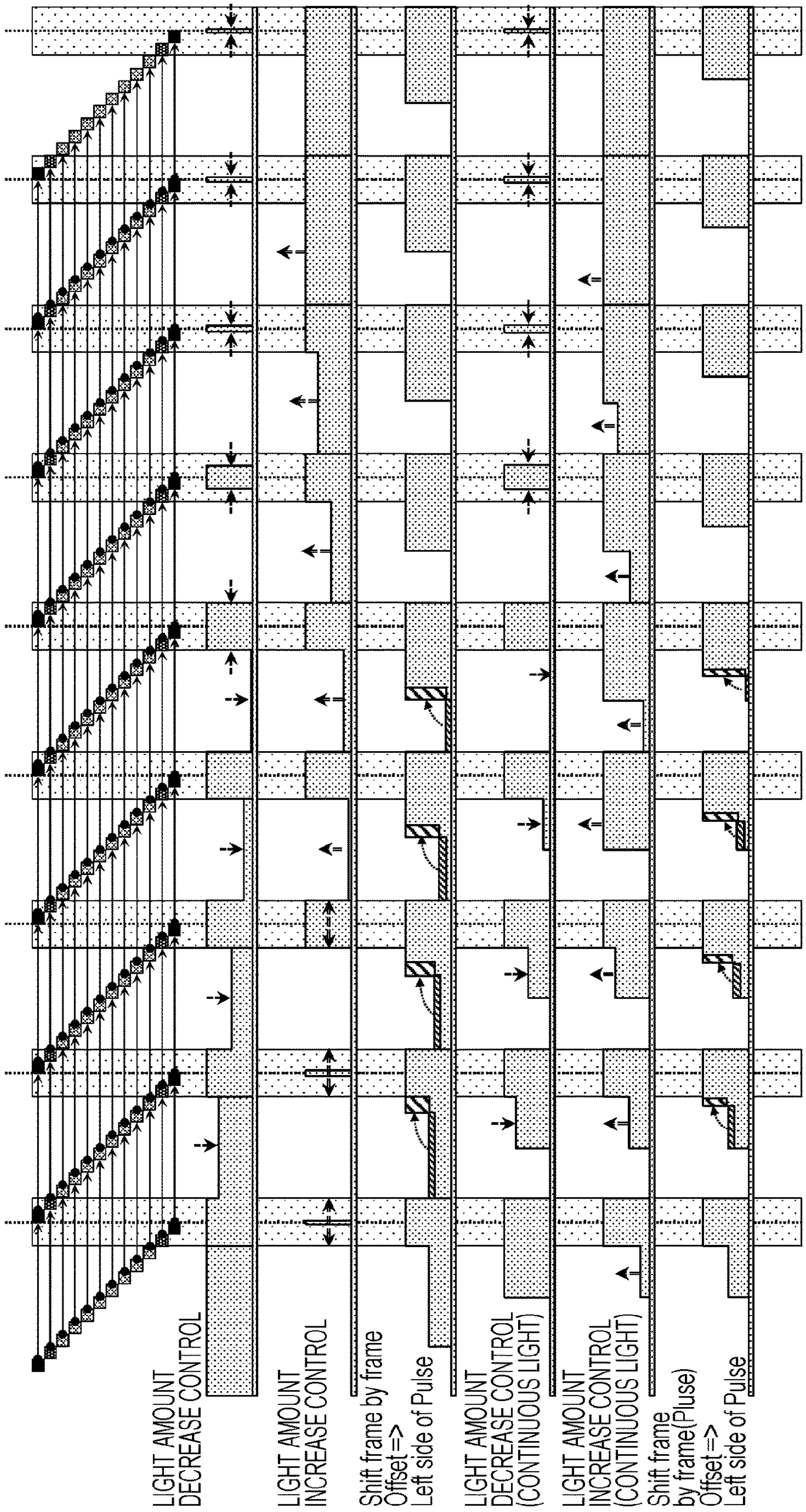
FIG. 15 is a diagram for explaining an offset light emission process (faint continuous light) in the non-light emission period (alternatively, the weak light emission period in which the light emission intensity is so weak that the light emission cannot be visually recognized).
Figure 16:
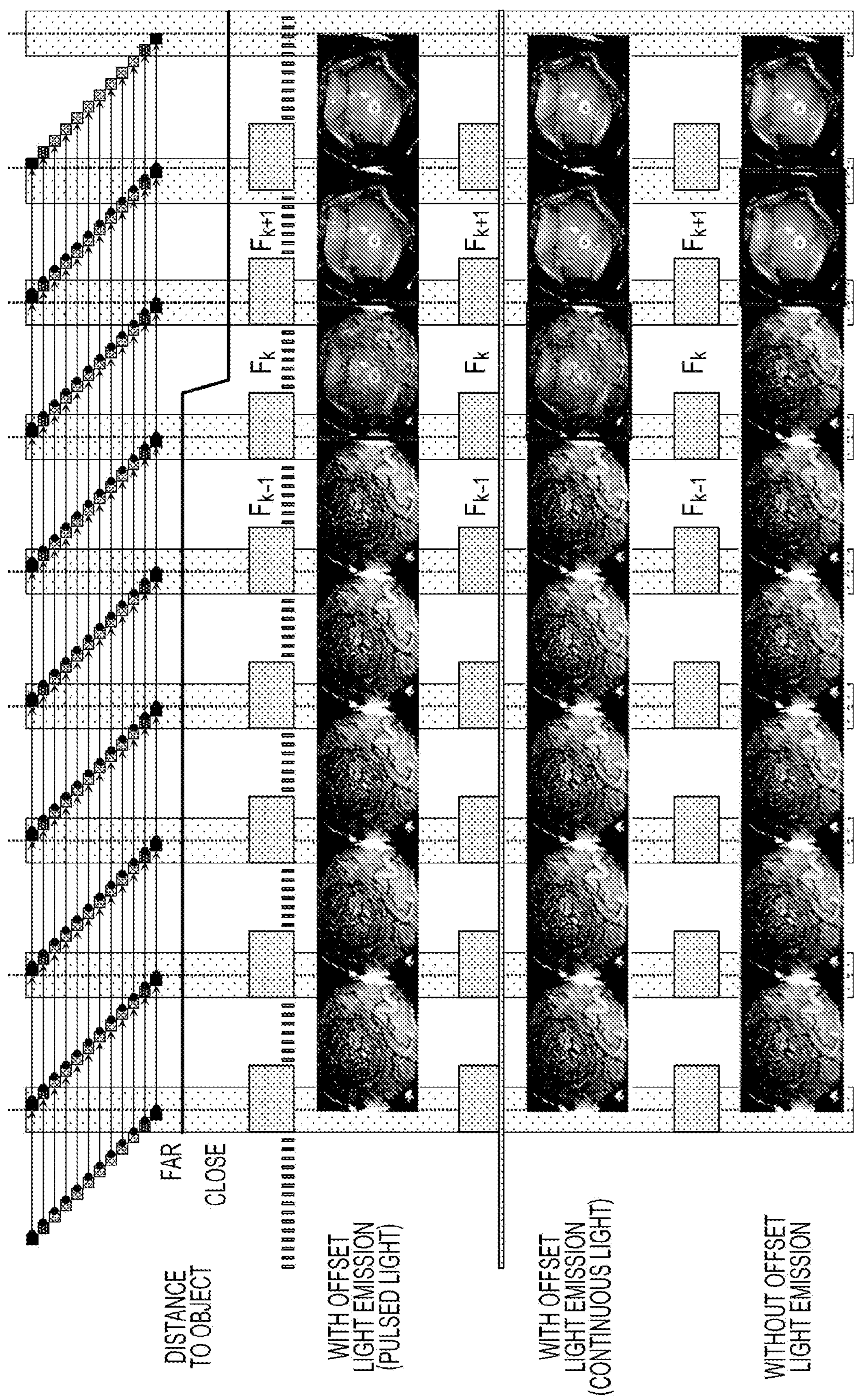
FIG. 16 is a diagram illustrating a difference in captured image that appears depending on the presence or absence of the offset light emission when the image sensor suddenly approaches an object.

FIGS. 14, 15, and 16 are diagrams for explaining an offset light emission process in a non-light emission period (alternatively, a weak light emission period in which the light emission intensity is so weak that the light emission cannot be visually recognized). FIG. 14 illustrates offset light emission by faint pulses. FIG. 15 illustrates offset light emission by faint continuous light. FIG. 16 is a diagram illustrating a difference in captured image that appears depending on the presence or absence of the offset light emission when the image sensor suddenly approaches the object. Here, “faint” means a light emission intensity that is sufficiently lower than the light emission intensity in the strong light emission period and does not generate the double-exposure image, but in a case where the object and the endoscope distal tip are close to each other, allows for imaging of the object at a brightness level at which the object can be visually recognized.

The offset light emission process is a process that is executed separately from the conventional light adjustment control process (FIG. 9 and the like) and the light adjustment control process according to the present embodiment (see FIGS. 11 and 13) (in the background of the light adjustment control process), and in which the faint offset light emission is performed during the non-light emission period. For the faint offset light emission, a mode in which pulsed light emission is performed (see FIG. 14) and a mode in which continuous light emission is performed (see FIG. 15) are considered, but a light emission pattern other than these modes may be used. For example, a light emission pattern may be configured by combining the pulsed light emission and the continuous light emission, or a light emission pattern with an irregular pulse width may be configured. Such faint offset light emission can be regarded as 0 (zero) in a case where the light emission intensity by the light adjustment control process (applicable to any light adjustment control process) is a predetermined value or higher. On the other hand, when the light emission intensity by the light adjustment control process is lower than the predetermined value (or when the light emission intensity is zero), the object is irradiated only with the offset light emission. As a result, an event occurring in the non-light emission period, which cannot be acquired as an image in principle, can be captured by the offset light emission.

FIG. 16 is a diagram illustrating the difference in captured image depending on the presence or absence of the faint offset light emission (pulsed light, continuous light) when the image sensor suddenly approaches the object. In a case where there is no faint offset light emission, the same image as that of a frame Fk−1 is acquired as the captured image of a frame Fk. On the other hand, in a case where the faint offset light emission is performed, the captured image of the frame Fk is clearly different from that of the frame Fk−1 in both cases of the pulsed light and the continuous light. It can be seen that an event when the image sensor suddenly approaches the object is captured in the frame Fk. In addition, it can be seen that the captured image of a frame Fk+1 does not differ depending on the presence or absence of the faint offset light emission.

<Light Adjustment Control Process: Flowchart>

Figure 17:
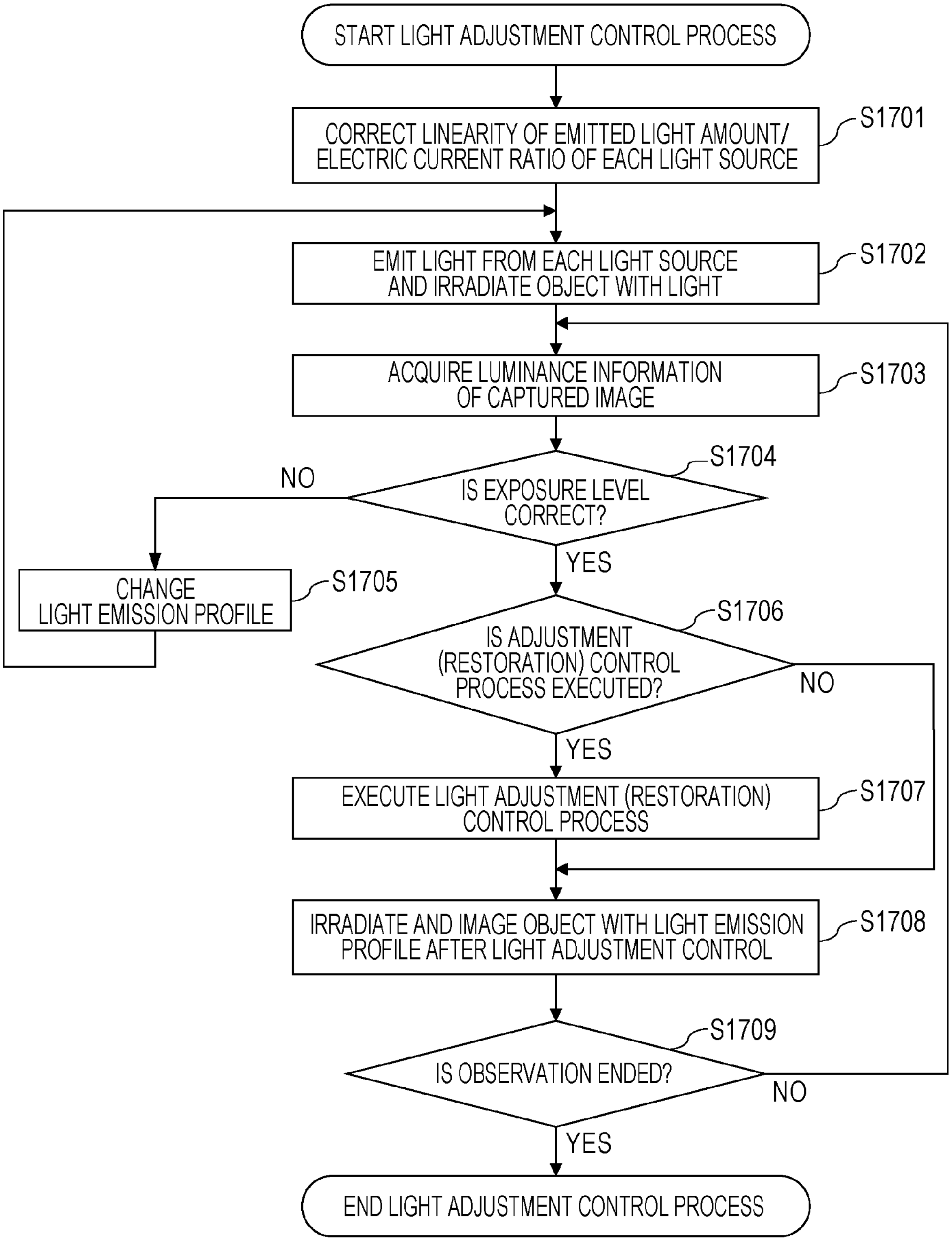
FIG. 17 is a flowchart for explaining the light adjustment control process according to the present embodiment.

FIG. 17 is a flowchart for explaining the light adjustment control process according to the present embodiment. The processes of the following respective steps are described by being mainly performed by the system controller 202. Other than this configuration, a control unit (processor) that performs operation control and arithmetic processing may be separately provided to execute the processes. Furthermore, the function of the system controller 202 may be provided to the light source control unit 2016 of the light source device 201. Therefore, the light adjustment (restoration) control process can be a part of the entire operation of the endoscope system 1 or can be a part of the operation of the light source device 201. In the latter case, the light source control unit 2016 mainly performs the processes of the respective steps.

(i) Step 1701

The light source control unit 2016 receives, from the system controller, the mode selection signal corresponding to the observation mode selected by the operator, and with respect to each light source (any combination of the green LED 2011 to the UV LED 2015) to emit light, corrects the linearity of the emitted light amount/electric current ratio of each light source using the above-described correction table.

(ii) Step 1702

The light source control unit 2016 generates illumination light by driving each light source to emit light with the drive current after the linearity correction of the emitted light amount/electric current ratio, and irradiates the object with the illumination light. Note that the light emission profile (the period of the strong light emission and the level and period of the weak light emission) at this time can be set to a predetermined value (default value), or the light emission profile used in the last operation in the previous use of the endoscope can be used.

(iii) Step 1703

The image sensor (for example, the CMOS sensor) of the imaging unit 103 detects reflected light from the object (observation site) generated by irradiating the object with the illumination light generated at step 1702, and transmits the captured image signal to the processor 200 via the scope connector circuit 401. The photometric unit 203 acquires the luminance information of the current captured image signal from the gain circuit included in the color conversion circuit 206, compares the acquired luminance information with the predetermined correct luminance value (for example, obtains a difference value), and passes this comparison result to the system controller 202. Note that the photometric unit 203 may acquire only the luminance information of the current captured image signal from the gain circuit, and another processing unit such as the system controller 202 may execute the comparison with the correct luminance value.

(iv) Step 1704

The system controller 202 compares the comparison result received from the photometric unit 203 (alternatively, the system controller 202 may calculate the comparison result (difference value)) with a predetermined threshold value (a threshold value for determining whether the exposure level is correct), and determines whether the current exposure level is correct. For example, when the comparison result (difference value) is equal to or lower than the predetermined threshold value, it can be determined that the current exposure level is correct. In a case where it is determined that the current exposure level is not correct (No at step 1704), the process proceeds to step 1705. On the other hand, in a case where it is determined that the current exposure level is correct (YES at step 1704), the process proceeds to step 1706.

(v) Step 1705

The system controller 202 changes the current light emission profile (information indicating the strong light emission period, the weak light emission period, and the weak light emission level) used for irradiating the object with the illumination light.

For example, in a case where the current exposure level is high and the image is too bright (in a case where the image is overexposed), the system controller 202 generates the exposure control signal so as to adjust the exposure level by lowering the weak light emission level in the light emission profile. In addition, in a case where the weak light emission level is zero in the current light emission profile, the system controller 202 generates the exposure control signal so as to adjust the exposure level by further shortening the strong light emission period.

On the other hand, in a case where the current exposure level is low and the image is too dark, the system controller 202 extends the strong light emission period when the strong light emission period does not reach a pseudo-global period width in the light emission profile. In addition, in a case where the strong light emission period in the current light emission profile reaches the pseudo-global period width, the system controller 202 generates the exposure control signal so as to adjust the exposure level by further raising the weak light emission level.

When the light emission profile is changed, the process proceeds to step 1702. Here, the light emission profile is gradually changed step by step to be adjusted to the correct exposure level. However, for example, information (for example, a table) indicating a relationship between a difference value (comparison value) between the luminance value of the captured image and the correct luminance value (the luminance value corresponding to the correct exposure level), and a change width of the light emission profile (information indicating how many steps the light emission profile is to be changed) may be stored in an internal memory (not illustrated) of the system controller 202, and an appropriate light emission profile may be directly obtained from the difference value (comparison value).

(vi) Step 1706

The system controller 202 determines whether it is necessary to execute the restoration control process on the light emission profile exhibiting the correct exposure level. The determination of whether it is necessary to perform the restoration control process can be made on the basis of, for example, whether the light emission profile has been changed after the previous execution of the restoration control process. When there is no change in the light emission profile, the object is currently imaged at the correct exposure level (correct brightness) and with the correct light adjustment (light adjustment in which no horizontal stripe appears). Therefore, it is not necessary to execute the restoration control process. On the other hand, when the light emission profile is changed, there is a possibility that the weak light emission component to be converted into the strong light emission is present. Therefore, the necessity of the restoration control process is determined depending on whether the changed light emission profile includes the weak light emission period.

In a case where it is determined that it is necessary to execute the restoration control process (YES at step 1706), the process proceeds to step 1707. On the other hand, in a case where it is determined that it is not necessary to execute the restoration control process (NO at step 1706), the process proceeds to step 1708.

(vii) Step 1707

The system controller 202 executes any of the process 1 to the process 3 in FIG. 11, to gradually convert the weak light emission component into the strong light emission component while maintaining the light emission integral value (light emission profile area), represented by "the strong light emission period×the strong light emission intensity+the weak light emission period×the weak light emission intensity", constant. For example, the restoration control process is executed by taking a time of about 1 second (a time equal to several tens of frames), and the light emission profile is changed to, for example, the light emission profile in FIG. 10 represented by Q1 to Q3. As a result, it is possible to acquire the image (FIG. 12E) with no double exposure and no horizontal stripe, from the image (FIG. 12A) in which the double exposure is performed and the horizontal stripe appears when only the exposure level is made correct.

(viii) Step 1708

The light source control unit 2016 receives the information of the light emission profile to be applied from the system controller 202, and generates the illumination light by emitting light from any of the LEDs 2011 to 2015 on the basis of the received light emission profile and the mode selection signal to irradiate the object with the illumination light. In addition, the image sensor (CMOS sensor) of the imaging unit 103 detects the reflected light from the object irradiated with the illumination light, generates the captured image signal, and transmits the captured image signal to the processor. Furthermore, the processor 200 executes predetermined image processing on the captured image signal to generate display image data, and displays the display image data on the screen of the monitor (display device) 300.

(ix) Step 1709

The system controller 202 determines whether an instruction to end the observation, for example, to end the imaging or turn off the illumination light, has been input from the operator. In a case where the instruction to end the observation has been input (YES at step 1709), the light adjustment control process ends. In a case where the instruction to end the observation has not been input (the instruction has not been detected) (NO at step 1709), the process proceeds to step 1703, and the determination/monitoring as to whether the current exposure level is correct, the light adjustment control process, and the like are continuously performed. The imaging unit 103 is installed at the distal tip 12 of the endoscope device 100 and moves in the body cavity of the subject. Therefore, the imaging unit 103 approaches or moves away from the object (observation site), so that the exposure level sometimes changes. Therefore, the operation of the light source device 201 is controlled so as to constantly monitor the luminance level of the captured image and maintain the correct exposure level.

Effects of Present Embodiment

According to the present embodiment, it is possible to image the object by ensuring a sufficient amount of light while avoiding rolling shutter distortions and artifacts. In addition, even when the change in the pulsed light emission period occurs over the rolling shutter period, the vertical movement of the horizontal stripe can be made less noticeable. Furthermore, in a case where the plurality of LEDs are simultaneously used as the light source, the ratio of the light amounts of the respective LEDs changes to cause the change in the dead mine and the change in the color when the light emission intensity changes unless the electric current control is performed by correcting the difference in the linearity of the emitted light amount/electric current ratio of each LED. However, the present embodiment can solve such a problem by restoring the light emission intensity in a short time.

<Specific Elements of Present Disclosure>

(1) Specific Element 1

A light source device that generates illumination light with which an object is irradiated, the light source device including:

a plurality of semiconductor light emitting elements that emit light beams having different wavelength bands from each other; and a control unit that controls a light emission profile of the plurality of semiconductor light emitting elements and drives the plurality of semiconductor light emitting elements, in which the light emission profile includes a strong light emission period in which light emission is performed with a predetermined light intensity and a weak light emission period in which light emission is performed with a light intensity weaker than the predetermined light intensity, and the control unit executes a restoration control process of converting a light emission amount in the weak light emission period into a light emission amount in the strong light emission period while maintaining a total amount of the light emission amount in the strong light emission period and the light emission amount in the weak light emission period constant.

(2) Specific Element 2

The light source device according to specific element 1, in which the control unit extends the strong light emission period by decreasing the light intensity in the weak light emission period and converting a light emission amount equal to the decreased intensity into the light emission amount in the strong light emission period while maintaining a length of the weak light emission period constant until the light intensity in the weak light emission period becomes zero.

(3) Specific Element 3

The light source device according to specific element 1, in which the control unit extends the strong light emission period by shortening the weak light emission period and converting a light emission amount equal to the shortened period into the light emission amount in the strong light emission period while maintaining the light intensity in the weak light emission period constant.

(4) Specific Element 4

The light source device according to specific element 1, in which the control unit extends the strong light emission period by shortening a length of the weak light emission period, and increasing the light intensity in the weak light emission period to convert the light emission amount in the weak light emission period as a light emission amount equal to the shortened period into the light emission amount in the strong light emission period.

(5) Specific Element 5

The light source device according to any one of specific elements 1 to 4, in which after determining a light emission profile where a luminance value in a captured image falls within a predetermined range, the control unit sets the determined light emission profile as a target for starting the restoration control process.

(6) Specific Element 6

The light source device according to any one of specific elements 1 to 5, in which the control unit further executes a process of correcting linearity of an emitted light amount/electric current ratio of the plurality of semiconductor light emitting elements.

(7) Specific Element 7

The light source device according to any one of specific elements 1 to 6, in which the control unit controls the plurality of semiconductor light emitting elements so as to perform offset light emission with a light emission intensity sufficiently lower than a light emission intensity in the strong light emission period but at a level enabling visual recognition during a non-light emission period other than the weak light emission period and the strong light emission period or during a weak light emission period in which a light emission intensity is so weak that light emission is not visually recognizable.

(8) Specific Element 8

The light source device according to specific element 7, in which the control unit executes the offset light emission with pulsed light or continuous light.

(9) Specific Element 9

An endoscope system that inserts an endoscope into an observation target and acquires an image of an object, the endoscope system including:

a plurality of semiconductor light emitting elements that emit light beams having different wavelength bands from each other;

an image sensor that irradiates the object with illumination light and detects reflected light from the object to generate an image signal;

a processor that processes the image signal to generate the image of the object and displays the image on a monitor; a main control unit that generates a control signal for controlling a light emission profile of the plurality of semiconductor light emitting elements on the basis of the image signal; and a light source control unit that receives the control signal from the main control unit and drives the plurality of semiconductor light emitting elements with a drive signal according to the light emission profile, in which the light emission profile includes a strong light emission period in which light emission is performed with a predetermined light intensity and a weak light emission period in which light emission is performed with a light intensity weaker than the predetermined light intensity, and the main control unit determines the light emission profile by executing a restoration control process of converting a light emission amount in the weak light emission period into a light emission amount in the strong light emission period while maintaining a total amount of the light emission amount in the strong light emission period and the light emission amount in the weak light emission period constant.

(10) Specific Element 10

The endoscope system according to specific element 9, in which the main control unit generates the control signal for extending the strong light emission period by decreasing the light intensity in the weak light emission period and converting a light emission amount equal to the decreased intensity into the light emission amount in the strong light emission period while maintaining a length of the weak light emission period constant until the light intensity in the weak light emission period becomes zero.

(11) Specific Element 11

The endoscope system according to specific element 9, in which the main control unit generates the control signal for extending the strong light emission period by shortening the weak light emission period and converting a light emission amount equal to the shortened period into the light emission amount in the strong light emission period while maintaining the light intensity in the weak light emission period constant.

(12) Specific Element 12

The endoscope system according to specific element 9, in which the main control unit generates the control signal for extending the strong light emission period by shortening a length of the weak light emission period, and increasing the light intensity in the weak light emission period to convert the light emission amount in the weak light emission period as a light emission amount equal to the shortened period into the light emission amount in the strong light emission period.

(13) Specific Element 13

The endoscope system according to any one of specific elements 9 to 12, further including a photometric unit that acquires luminance value information using the image signal, in which the main control unit acquires the luminance information from the photometric unit, determines a light emission profile where a luminance value in the image signal falls within a predetermined range, and sets the determined light emission profile as a target for starting the restoration control process.

(14) Specific Element 14

The endoscope system according to any one of specific elements 9 to 13, in which the main control unit further generates a control signal for controlling the plurality of semiconductor light emitting elements so as to perform offset light emission with a light emission intensity sufficiently lower than a light emission intensity in the strong light emission period but at a level enabling visual recognition during a non-light emission period other than the weak light emission period and the strong light emission period or during a weak light emission period in which a light emission intensity is so weak that light emission is not visually recognizable, and outputs the control signal to the light source control unit.

REFERENCE SIGNS LIST

1 Endoscope system
100 Endoscope device
103 Imaging unit
200 Processor
201 Light source device
2011 Green LED
2012 Blue LED
2013 Red LED
2014 Amber LED
2015 UV LED
2016 Light source control unit
2017, 2018 Cross prism
202 System controller
203 Photometric unit
300 Monitor

The invention claimed is:

1. A light source device that generates illumination light with which an object is irradiated, the light source device comprising:

a plurality of semiconductor light emitting elements that emit light beams having different wavelength bands from each other; and a control unit that controls a light emission profile of the plurality of semiconductor light emitting elements and drives the plurality of semiconductor light emitting elements, wherein the light emission profile includes a strong light emission period in which light emission is performed with a predetermined light intensity and a weak light emission period in which light emission is performed with a light intensity weaker than the predetermined light intensity, and the control unit executes a restoration control process of converting a light emission amount in the weak light emission period into a light emission amount in the strong light emission period while maintaining a total amount of the light emission amount in the strong light emission period and the light emission amount in the weak light emission period constant.

2. The light source device according to claim 1, wherein the control unit extends the strong light emission period by decreasing the light intensity in the weak light emission period and converting a light emission amount equal to the decreased intensity into the light emission amount in the strong light emission period while maintaining a length of the weak light emission period constant until the light intensity in the weak light emission period becomes zero.

3. The light source device according to claim 1, wherein the control unit extends the strong light emission period by shortening the weak light emission period and converting a light emission amount equal to the shortened period into the light emission amount in the strong light emission period while maintaining the light intensity in the weak light emission period constant.

4. The light source device according to claim 1, wherein the control unit extends the strong light emission period by shortening a length of the weak light emission period, and increasing the light intensity in the weak light emission period to convert the light emission amount in the weak light emission period as a light emission amount equal to the shortened period into the light emission amount in the strong light emission period.

5. The light source device according to claim 1, wherein after determining a light emission profile where a luminance value in a captured image falls within a predetermined range, the control unit sets the determined light emission profile as a target for starting the restoration control process.

6. The light source device according to claim 1, wherein the control unit simultaneously executes a process of determining a light emission profile where a luminance value in a captured image falls within a predetermined range, and the restoration control process performed on the light emission profile.

7. The light source device according to claim 1, wherein the control unit further executes a process of correcting linearity of an emitted light amount/electric current ratio of the plurality of semiconductor light emitting elements.

8. The light source device according to claim 1, wherein the control unit controls the plurality of semiconductor light emitting elements so as to perform offset light emission with a light emission intensity that is sufficiently lower than a light emission intensity in the strong light emission period and does not generate a double-exposure image, but in a case where the object is close, allows the object to be visually recognized during a non-light emission period other than the weak light emission period and the strong light emission period or during a weak light emission period in which a light emission intensity is so weak that light emission is not visually recognizable.

9. The light source device according to claim 8, wherein the control unit executes the offset light emission with pulsed light or continuous light.

10. An endoscope system that inserts an endoscope into an observation target and acquires an image of an object, the endoscope system comprising:

a plurality of semiconductor light emitting elements that emit light beams having different wavelength bands from each other;

an image sensor that irradiates the object with illumination light and detects reflected light from the object to generate an image signal;

a processor that processes the image signal to generate the image of the object and displays the image on a monitor; a main control unit that generates a control signal for controlling a light emission profile of the plurality of semiconductor light emitting elements on the basis of the image signal; and a light source control unit that receives the control signal from the main control unit and drives the plurality of semiconductor light emitting elements with a drive signal according to the light emission profile, wherein the light emission profile includes a strong light emission period in which light emission is performed with a predetermined light intensity and a weak light emission period in which light emission is performed with a light intensity weaker than the predetermined light intensity, and the main control unit determines the light emission profile by executing a restoration control process of converting a light emission amount in the weak light emission period into a light emission amount in the strong light emission period while maintaining a total amount of the light emission amount in the strong light emission period and the light emission amount in the weak light emission period constant.

11. The endoscope system according to claim 10, wherein the main control unit generates the control signal for extending the strong light emission period by decreasing the light intensity in the weak light emission period and converting a light emission amount equal to the decreased intensity into the light emission amount in the strong light emission period while maintaining a length of the weak light emission period constant until the light intensity in the weak light emission period becomes zero.

12. The endoscope system according to claim 10, wherein the main control unit generates the control signal for extending the strong light emission period by shortening the weak light emission period and converting a light emission amount equal to the shortened period into the light emission amount in the strong light emission period while maintaining the light intensity in the weak light emission period constant.

13. The endoscope system according to claim 10, wherein the main control unit generates the control signal for extending the strong light emission period by shortening a length of the weak light emission period, and increasing the light intensity in the weak light emission period to convert the light emission amount in the weak light emission period as a light emission amount equal to the shortened period into the light emission amount in the strong light emission period.

14. The endoscope system according to claim 10, further comprising a photometric unit that acquires luminance value information using the image signal, wherein the main control unit acquires the luminance value information from the photometric unit, determines a light emission profile where a luminance value in the image signal falls within a predetermined range, and sets the determined light emission profile as a target for starting the restoration control process.

15. The endoscope system according to claim 10, wherein the main control unit further generates a control signal for controlling the plurality of semiconductor light emitting elements so as to perform offset light emission with a light emission intensity that is sufficiently lower than a light emission intensity in the strong light emission period and does not generate a double-exposure image, but in a case where the object is close, allows the object to be visually recognized during a non-light emission period other than the weak light emission period and the strong light emission period or during a weak light emission period in which a light emission intensity is so weak that light emission is not visually recognizable, and outputs the control signal to the light source control unit.

* * * * *